United States Patent
Davidson et al.

(10) Patent No.: US 12,005,155 B2
(45) Date of Patent: Jun. 11, 2024

(54) HIGH-MODULUS ALLOY FOR MEDICAL DEVICES

(71) Applicant: Warsaw Orthopedic, Inc., Warsaw, IN (US)

(72) Inventors: James Davidson, San Juan Capistrano, CA (US); William Rezach, Covington, TN (US); Rodney Ballard, Lakeland, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 595 days.

(21) Appl. No.: 17/113,635

(22) Filed: Dec. 7, 2020

(65) Prior Publication Data

US 2021/0220513 A1 Jul. 22, 2021

Related U.S. Application Data

(60) Provisional application No. 62/964,578, filed on Jan. 22, 2020.

(51) Int. Cl.
| | | |
|---|---|---|
| *A61L 31/02* | (2006.01) | |
| *A61L 27/04* | (2006.01) | |
| *A61L 27/50* | (2006.01) | |
| *A61L 31/14* | (2006.01) | |
| *C22C 27/00* | (2006.01) | |
| *C22C 27/04* | (2006.01) | |

(52) U.S. Cl.
CPC .............. *A61L 27/047* (2013.01); *A61L 27/50* (2013.01); *A61L 31/022* (2013.01); *A61L 31/14* (2013.01); *C22C 27/00* (2013.01); *C22C 27/04* (2013.01); *A61L 2430/12* (2013.01); *A61L 2430/22* (2013.01); *A61L 2430/38* (2013.01)

(58) Field of Classification Search
CPC .............................. C22C 27/00; A61L 31/022
See application file for complete search history.

(56) References Cited

U.S. PATENT DOCUMENTS

| | | | | |
|---|---|---|---|---|
| 3,186,837 A | * | 6/1965 | Duffek, Jr. .............. | C22C 27/02 420/580 |
| 5,372,661 A | | 12/1994 | Felix et al. | |
| 2016/0237541 A1 | * | 8/2016 | Patel ..................... | B21C 23/002 |

FOREIGN PATENT DOCUMENTS

| | | |
|---|---|---|
| AT | 343403 T | 11/2006 |
| CN | 101415374 A | 4/2009 |
| CN | 101921929 A | 12/2010 |
| CN | 102170923 A | 8/2011 |
| CN | 105247092 A | 1/2016 |
| WO | 93016206 A1 | 8/1993 |

OTHER PUBLICATIONS

Office Action in Chinese Application No. 202080094080.5 dated Feb. 13, 2023.
A Shah Idil, et al., The Use of Tungsten as a Chronically Implaned Material, Journal of Neural Engineering, 15 (2018) 021006 (13Pp), https://doi.org/10.1088/1741-2552/aaa502.
Lassner, et al., Tungsten Properties, Chemistry, Technology of the Element, Alloys, and Chemical Compounds, 1999 Kluwer Academic / Plenum Publishers, New York, 447 Pp.
Doulgeris, James, Biomechanical Comparison of Titanium and Cobalt Chromium Pedicle Screw Rods in an Unstable Cadaveric Lumbar Spine, University of South Florida Graduate School, (2013) Graduate Theses and Dissertations, http://scholarcommons.usf.edu/etd/4812, 60 Pp.
Jaffee, et al., The Effect of Rhenium on the Fabricability and Ductility of Molybdenum and Tungsten, Battelle Memorial Institute, Technical Report, (1958), 49 Pp.
Davydov, et al., Determination of Corosion Rate of Rhenium and Its Alloys, Chemical Engineering Transactions, vol. 41, 2014, www.aidic.it/cet, 6Pp.
Schmidt, et al., The Engineering Properties of Molyvdenum and Molybdnum Alloys, Defense Metals Information Center Report 190, Battelle Memorial Institute, Sep. 20, 1963, 291 Pp.
Eliaz, Noam, Corrosion of Metallis Biomaterials; a Review, Department of Materials Science and Enginnering, Tele-Aviv University, Jan. 28, 2019, www.mdpi.com/journal/materials, 91 Pp.
Schmidt, et al., The Engineering Properties of Molyvdenum and M0lybdnummetals Information Center Report 191, Battelle Memorial Institute, Sep. 27, 1963, 141 Pp.
Office Action in Chinese Application No. 202080094080.5 dated Jul. 22, 2023.
Debatin et al., Interventional Magnetic Resonance Imaging, 20011231, Springer-Verlag Berlin Heidelberg 1998, ISBN 7-117-04057-2/R 4058.

* cited by examiner

*Primary Examiner* — Alexandra M Moore
(74) *Attorney, Agent, or Firm* — FOX ROTHSCHILD LLP

(57) ABSTRACT

Medical devices, such as implants, having a high-modulus alloy. The alloy includes a biocompatible refractory-metal-based alloy having multiple refractory metals. The alloy has an elastic modulus above about 300 GPa. The alloy comprises 30-35% tungsten, 60% molybdenum, and 5-10% niobium. The alloy is absent of rhenium.

35 Claims, 39 Drawing Sheets

| Material | UNS Designation | $\sigma_{UTS}$ (MPa) | $\sigma_{YP}$ (MPa) | E (GPa) | ε (%) |
|---|---|---|---|---|---|
| 316L, annealed | S31673 | min 490 | min 190 | 190 | min 40 |
| 316L, cold worked | S31673 | min 860 | min 690 | 190 | min 10 |
| BioDur® 108 stainless steel, annealed | S29108 | min 827 | min 517 | – | min 30 |
| Co-28Cr-6Mo, as-cast | R30075 | min 655 | min 450 | 210 | min 8 |
| Co-28Cr-6Mo, forged | R31537 | min 1172 | min 827 | 210 | min 12 |
| Co-20Cr-15W-10Ni, annealed | R30605 | min 860 | min 310 | 210 | min 30 |
| Co-35Ni-20Cr-10Mo, solution annealed | R30035 | 793-1000 | 241-448 | 232 | min 50 |
| CP-Ti, grade 1 | R50250 | min 240 | min 170 | 110 | min 24 |
| CP-Ti, grade 4 | R50700 | min 550 | min 483 | 110 | min 15 |
| Ti-6Al-4V ELI, annealed | R56401 | min 825 | min 760 | 116 | min 8 |
| Ti-6Al-7Nb, annealed | R56700 | min 900 | min 800 | 114 | min 10 |
| Ti-13Nb-13Zr, capability aged | R58130 | min 860 | min 725 | 75 | min 8 |
| Ti-12Mo-6Zr-2Fe, solution-annealed | R58120 | min 932 | min 897 | 74-85 | min 12 |
| Ni-Ti, annealed | – | min 551 | – | 40 | min 10 |
| Cortical bone | – | 70-150 | 30-70 | 10-30 | 0-8 |

FIG. 1

(Prior Art)

| TREATMENT | Tensile Strength, min | | Yield Strength (0.2 % offset), min | | Elongation in 4D or 4W, min (where D is specimen diam. & W is specimen width) | Reduction in Area, min | Hardness, typical (not for inspection) |
|---|---|---|---|---|---|---|---|
| | ksi | MPa | ksi | MPa | % | % | Rockwell |
| ANNEALED | 130 | 897 | 75 | 517 | 20 | 20 | C25 |
| HOT WORKED | 145 | 1000 | 101 | 700 | 12 | 12 | C28 |
| COLD WORKED | 145 | 1000 | 101 | 700 | 12 | 12 | C28 |
| WARM WORKED | 170 | 1192 | 120 | 827 | 12 | 12 | C35 |

| Property | Niobium | Molybdenum | Tantalum | Tungsten | Rhenium | Hafnium | Zirconium |
|---|---|---|---|---|---|---|---|
| Melting Point (C) | 2477 | 2623 | 3017 | 3422 | 3186 | 2220 | 2130 |
| Density (g/m3) | 8.57 | 10.3 | 16.7 | 19.3 | 21.0 | 13.31 | 7.18 |
| Approx. Rc Hardness | 40 | 35 | 45 | 65 | 65 | 35 | 70 |
| Tensile Str. (MPa) | 207-345 | 827-1329 | 240-480 | 690-3445 | 1070 | 450 | 430 |
| Elastic Modulus (GPa) | 105 | 329 | 186 | 411 | 463 | 138 | 248 |
| Magnetic Susceptibility | +195 | -97 | +130 | +59 | +68 | +85 | +180 |
| cost/Kg | $43 | $26 | $160 | $30 | $2844 | $1000 | $7.2 |

FIG. 14
(Prior Art)

| Impact category | Ta | Re | W | Nb | Mo |
|---|---|---|---|---|---|
| Global warming potential (kg $CO_2$ eq / kg) | 260 | 450 | 12.6 | 12.5 | 5.7 |
| Cumulative energy demand (MJ eq / kg) | 4,360 | 9,040 | 133 | 172 | 117 |
| Terrestrial acidification (kg $SO_2$ eq / kg) | 1.7 | 11 | 0.29 | 0.053 | 0.16 |
| Freshwater eutrophication (kg P eq / kg) | 1.5E-01 | 3.5E+01 | 9.3E-6 | 3.7E-03 | 0.54 |
| Human toxicity (CTUh/kg) | 1.2E-04 | 5.9E-02 | 3.4E-05 | 6.4E-06 | 9 E-04 |

FIG. 15
(Prior Art)

| No | Proposed alloy | Reason reviewed or tested | Est. UTS (MPa) | Est. Mod. (GPa) | Est. Elong. % | Base $cost/kg |
|---|---|---|---|---|---|---|
| Ref. | CoCrMo rods | Reference | 900-1100 | 220 | 20-12 | 32 |
| Ref. | TZM (~100%Mo) | Reference | 900 | 325 | 10-15% | 26 |
| Ref. | Mo-47.5Re | MiRus Inc. | 1100 | 365 | 23% | 1380 |
| Ref. | Mo-25W | Battelle Ref. Stress relieved | 930-1000 | 350 | 5-12 | 27 |
| Ref. | Mo-30W | Battelle Ref. Stress relieved | 835 | 345 | 26 | 27 |
| Ref. | Mo-50W | Battelle Ref. Stress relieved | 993 | 370 | 50 | 28 |
| 1 | 30Mo70W | Base High-Str. Corr/Duct.info | 1200 | 385 | 5% | 29 |
| 2 | 70Mo30W(literature) | Base Lower Str. Corr/Duct | 700 | 353 | 20% | 27 |
| 3 | 70Mo20W10Cr | Less Ductile + Corrosion resistance | 800 | 337 | 10% | 26 |
| 4 | 40Mo50W10Cr | Strength and Corrosion promoted | 1000 | 363 | 2-3% | 26 |
| 5 | 30Mo60W10Cr | W may ++ strength | 1200 | 371 | 1-2% | 27 |
| 6 | 60Mo30W10Cr | Less W may up ductility & lower strength | 800 | 345 | 6% | 26 |
| 7 | 60Mo20W20Cr | More Cr may create self-passivation | 900 | 329 | 3% | 25 |
| 8 | 60Mo30W10Ta | Ta ups ductility and may obviate including Cr | 900 | 339 | 8% | 40 |
| 9 | 65Mo30W5Ta | 5Ta may up corrosion resistance and ductility | 800 | 346 | 10 | 34 |
| 10 | 60Mo30W10Nb | Same as 7 and 8, and Nb may add benefits | 900 | 331 | 15% | 29 |
| 11 | 60Mo35W5Nb | Same as 9, but with less Nb | 800 | 346 | 15 | 27 |
| 12 | 50Mo40W5Cr5Nb | Cr+Nb may affect ductility & corrosion resist. | 1000 | 346 | 8 | 27 |
| 13 | 60Mo35W5Hf | Incr. ductility | 900 | 348 | 12 | 76 |

FIG. 27

| Metal | Nb | Mo | Ta | W | Re | Hf | Cr |
|---|---|---|---|---|---|---|---|
| Magnetic susceptibility | +195 | -97 | +130 | +59 | +68 | +85 | +180 |

FIG. 28
(Prior Art)

Standard Free Energies of Formation at 1000K of
Some Oxides Whose Metallic Elements Are
Often Present in Superalloys

| Element | $\Delta G°$ (k joule/g atom oxygen) |
|---|---|
| Hf | 459.6 ($HfO_2$) |
| Al | 453.7 ($Al_2O_3$) |
| Zr | 451.8 ($ZrO_2$) |
| Ti | 381.7 ($TiO_2$) |
| Si | 348.9 ($SiO_2$) |
| Ta | 321.0 ($Ta_2O_5$) |
| Mn | 311.9 (MnO) |
| Nb | 308.4 ($Nb_2O_5$) |
| Cr | 291.7 ($Cr_2O_3$) |
| Mo | 303.7 ($MoO_2$) |
| W | 200.6 ($WO_2$) |
| Fe | 198.9 (FeO) |
| Co | 163.2 (CoO) |
| Ni | 150.3 (NiO) |

FIG. 39
(Prior Art)

HIGH-MODULUS ALLOY FOR MEDICAL DEVICES

CROSS-REFERENCE TO RELATED APPLICATION

This application claims the benefit of and priority to U.S. Provisional Patent Application No. 62/964,578 filed Jan. 22, 2020, the entire disclosure of which is incorporated by reference herein.

FIELD

The present technology is related generally to medical devices, and more particularly to high-modulus alloys for medical devices.

BACKGROUND

For surgical implants, it is desirable to minimize device profile and increase stiffness, or elastic modulus of the implant. An example implant procedure is implants for spinal fusion or correction.

Stiffness tends to minimize motion and optimize stability of the spine segments being joined or otherwise secured.

Materials are desired having sufficient stiffness and acceptable corrosion resistance.

Co—Cr—Mo alloys and austenitic stainless steel (304I, 316L), and low-modulus titanium alloys (Ti6Al4V, etc.), are example materials on the market.

Better-performing materials within desired cost are desired for medical implants.

SUMMARY

The systems, process, and techniques of this disclosure relate generally to a high-modulus alloy for medical devices, such as medical implants.

In various aspects, the present disclosure provides a medical device, such as an implant or device, having a high-modulus alloy. The alloy includes a biocompatible refractory-metal-based alloy having multiple refractory metals. The alloy in various embodiments has an elastic modulus above about 300 GPa, and includes tungsten, molybdenum, and tungsten.

In other aspects, the present disclosure provides methods for melting and forming any of the alloys claimed above or described further above herein.

BRIEF DESCRIPTION OF DRAWINGS

FIG. 1 shows strength and modulus values for various implant alloys.

FIG. 10 shows a table of mechanical test requirements, corresponding to Type 01 and Type 02.

FIG. 13 shows a periodic table highlighting groups referred to as refractory elements.

FIG. 14 is a table showing values for various properties, for select materials.

FIG. 15 is a table comparing refractory metals in terms of environmental impact. Reference is made here to a publication, Life Cycle Assessment of Metals: A Scientific Synthesys paper, Nuss P & Eckelman MJ, 2014).

FIG. 27 is a table showing properties for various materials.

FIG. 28 is a table showing values for magnetic susceptibility ($X10^{-6}$ ppm) for elemental options for alloys of the present disclosure, for various embodiments.

FIG. 39 is a table showing standard free energies of formation at 100K of some oxides having select metallic elements often present in superalloys.

DETAILED DESCRIPTION

Figure 2:
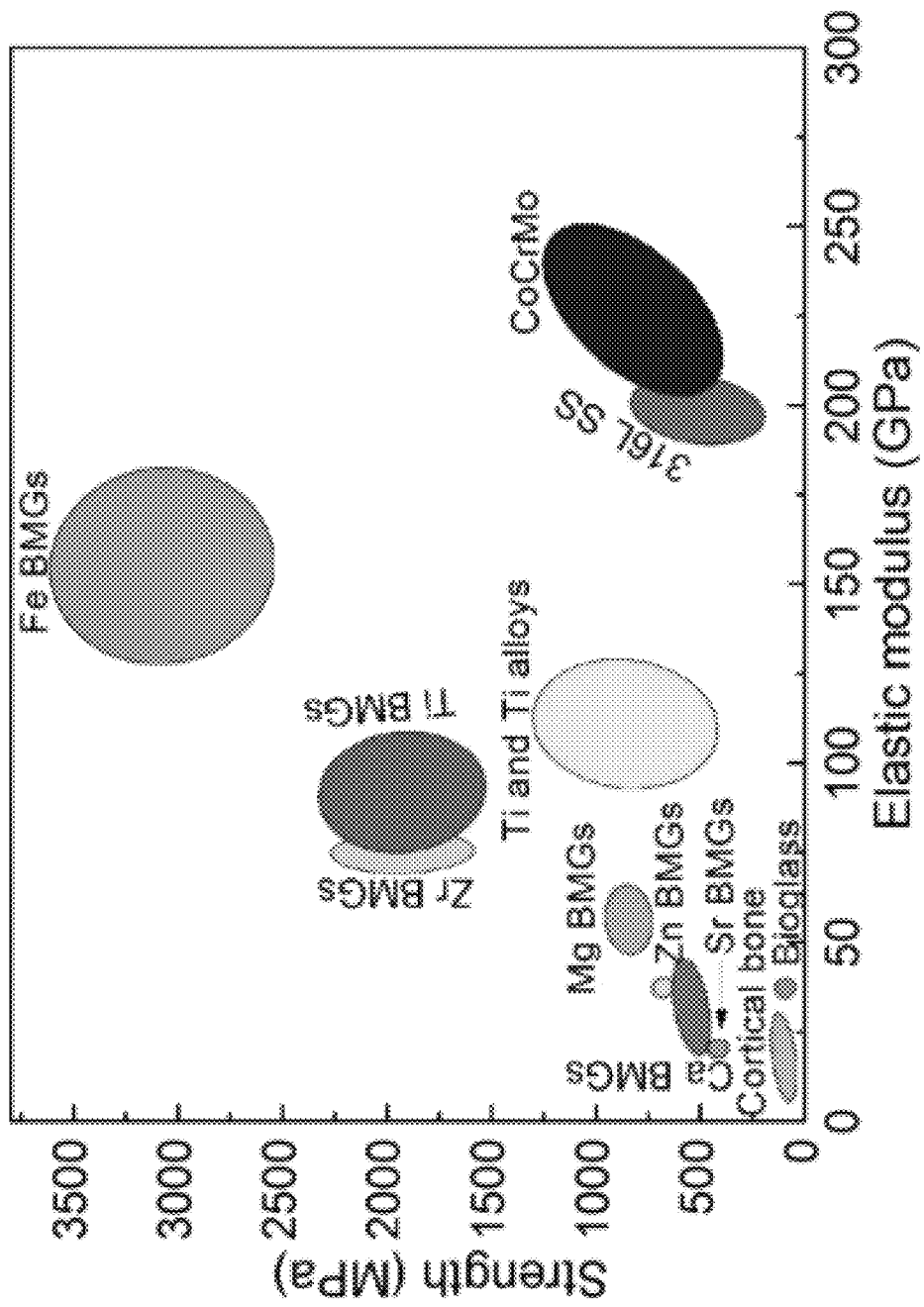
FIG. 2 shows strength versus modulus for various materials. The view can be referred to as an Ashby diagram. It compares these mechanical properties of conventional bioglasses, biometals and biomedical BMGs.

In spinal fusion, correction, and other implant procedures, it is desirable as provided to minimize device profile and increase stiffness (elastic modulus) of the implant, while maintaining acceptable corrosion resistance, comparable to currently used Co—Cr—Mo alloys and austenitic stainless steel (304I, 316L). Stiffness tends to minimize motion and optimize stability of the spine segments being joined or otherwise secured.'

Inclusion of sufficient chromium in the alloy of the present technology provides acceptable passivity and corrosion resistance, which is important in the aqueous-chloride environment of the patient body. The high modulus of the new alloys of the present technology are in various embodiments achieved by use of one or more select elements, such as tungsten and molybdenum, as a major portion of the alloy composition.

It is also desirable for the alloy of the present technology to have a reasonable cost. Relatively expensive materials such as Re can be avoided, for instance.

It is in some embodiments desired for the alloy of the present technology to have low imaging artifact, particularly for MRI, CT and other imaging. Example material types that produce high levels of undesirable imaging artifact include paramagnetic or non-ferromagnetic. Cobalt, Iron, and Nickel are highly ferromagnetic elements and so in some embodiments are avoided or limited, and, thus, not included in the invention alloys.

Candidate alternative metals and alloys for inclusion in the present technology can satisfy such next-generation spinal-implant requirements.

The materials of the present technology can be used in various applications, such as surgical devices, more particularly surgical implants, such as dental or spinal implants, such as spinal plates, spinal rods, spinal screws, screw heads (e.g., receivers, or tulips, and any extenders or tabs connected thereto), and connectors.

Thus, in addition to implementation in spinal plates and rods, there is also value in screw heads also having a high (higher, e.g., higher than standard) modulus material. Benefits for the screw head include mitigation of screw-head splay, which is the undesired opening/deflection of head arms forming a rod slot holding the spinal rod correcting the spine. A harder, higher-modulus alloy would also reduce micro-fretting between the screw head and plate and/or anchor.

Surgery for spinal deformity in many cases involves the use of segmental fixation with rigid implants and instrumentation for surgical manipulation and correction of the spine. Pedicle screws and rods are implanted along multiple vertebral body segments, with rods assembled and locked in placed to form a rigid construct along the spine. The construct acts a leverage to de-rotate and bend, or at least to hold, the spine in a more normal curvature.

Considering the forces required to correct the deformity, the rods and screw heads used to create the construct need to be rigid enough to withstand the loading applied during correction and post-operation use without undergoing undesirable deformation resulting in screw head splaying or rod flexing. This can be accomplished by relatively high stiffness metals and robust-sized components to ensure sufficient rigidity. Large size components can, though, result in a bulky construct that protrudes into the skin after closure of the surgical site, leading to issues with cosmesis and surgical site pain.

The ability to reduce the size of these components to allow for lower-profile constructs would enhance value of the implants used for these procedures and improve patient response post-surgery. One method to reduce profile without undesirably sacrificing rigidity or stiffness, or without sacrificing rigidity or stiffness at all, is to use one or more ultra-high stiffness materials. This allows for a smaller implant to sufficiently resist expected deformation forces, such as under bending for, during, or after the implantation procedure.

Minimizing significant plasticity and the amount of non-linear force vs. displacement behavior is also important to match performance. This is because total deformation of a smaller geometric component will be higher for a given applied load.

TZM Alloy

An example conventional alloy is a Molybdenum alloy, e.g., TZM, containing 0.5 wt. % Ti, 0.08 wt % Zr, and with 0.02% Carbon. The mechanical properties are as follows:
UTS=760-965 MPa
Yield Str.=860 MPa
Elastic Modulus=320-325 GPa
Elongation=10-15%
Hardness=220 DPH This alloy, as for almost all refractory metal alloys, has high temperature, high-strength creep, and oxidation-resistant applications. Because the composition is essentially all molybdenum, the corrosion resistance in an aqueous chloride environment is poor, though.

Turning now to the figures, and more particularly the first figure, various existing implant alloys are shown in the table of FIG. 1. The figure shows strength and modulus values for various current implant alloys. As shown, the maximum elastic modulus is about 230 GPa.

FIG. 2 shows strength versus modulus for various materials. The view can be referred to as an Ashby diagram. It compares these mechanical properties of conventional bioglasses, biometals and biomedical BMGs. (From Elseveir).

Figure 3:
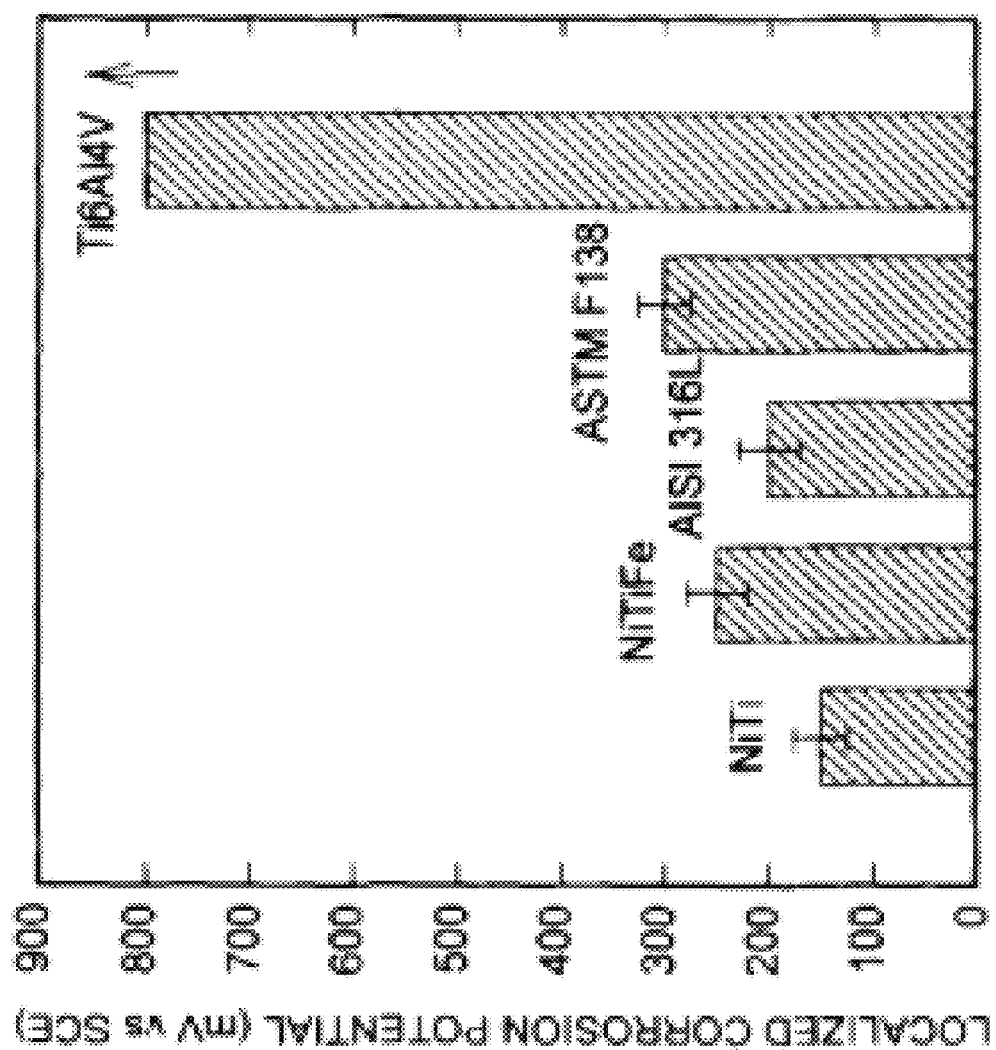
FIG. 3 is a table showing values for localized corrosion potential (mV vs SCE) for various materials. The tests included modified ASTM F746 tests on mechanically polished surface in 0.9% NaCl solution at 37 degrees C. Data are reproduced.

Corrosion resistance of current implant alloys is shown in FIG. 3. The figured is a table showing values for localized corrosion potential (mV vs SCE) for various materials. The tests included modified ASTM F746 tests on mechanically polished surface in 0.9% NaCl solution at 37 degrees C. It is desirable to have an implant alloy with the corrosion potential, in an aqueous chloride environment, to be greater than about 150 mV, and preferably above about 300 mV.

Figure 4:
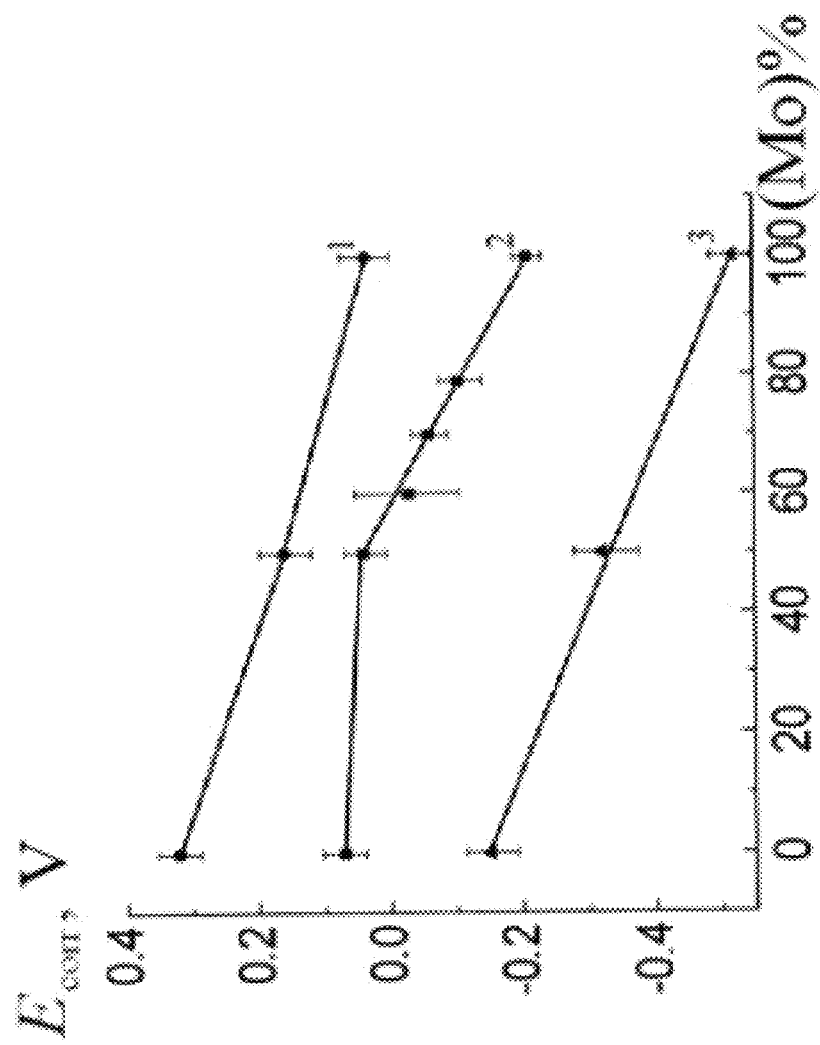
FIG. 4 is a line chart showing dependences of corrosion potential on the composition of a test specimen in the solutions (1) 0.5 M NaCl+0.1 M HCl, (2) 0.5 M NaCl, and (3) 0.5 M NaCl+0.1 M NaOH.

FIG. 4 is a line chart showing dependences of corrosion potential on the composition of a test specimen in the solutions (1) 0.5 M NaCl+0.1 M HCl, (2) 0.5 M NaCl, and (3) 0.5 M NaCl+0.1 M NaOH. The figure shows that the corrosion resistance of molybdenum is in aqueous chloride solution is poor. Although the addition of Rhenium can improve this corrosion resistance, the corrosion potential is still less than 100 my (even pure Re). Thus, rhenium is not the preferred alloy element, and the addition of chromium, greater than about 5% is preferred in various embodiments of the alloy.

The presence of sufficient levels of chromium provides a passive and protective chromium oxide protective surface layer, just as it protects the corrosion of iron in stainless steels and the corrosion of cobalt in CoCrMo and other cobalt alloys. Alternatively, or in combination with chromium, the addition of elements with highly passive oxides (Ti, Zr, Nb, Ta, Hf) can also help improve the corrosion resistance of the base metal. But, as for the case of the lower-modulus chromium, these lower-modulus elements will reduce the overall desired high modulus of the alloy according to the present technology.

Below are various examples of spinal rods, plates, anchors and screws that are expected to benefit for the current alloys according to the present technology. However, other spinal and orthopaedic implant, and dental devices are within the scope of this patent, as are medical devices such as cutting instruments, wear-resistant drill guides, arthroscopy devices and cannulation, torque-responsive guidewires and catheters, and the like.

Figure 5:
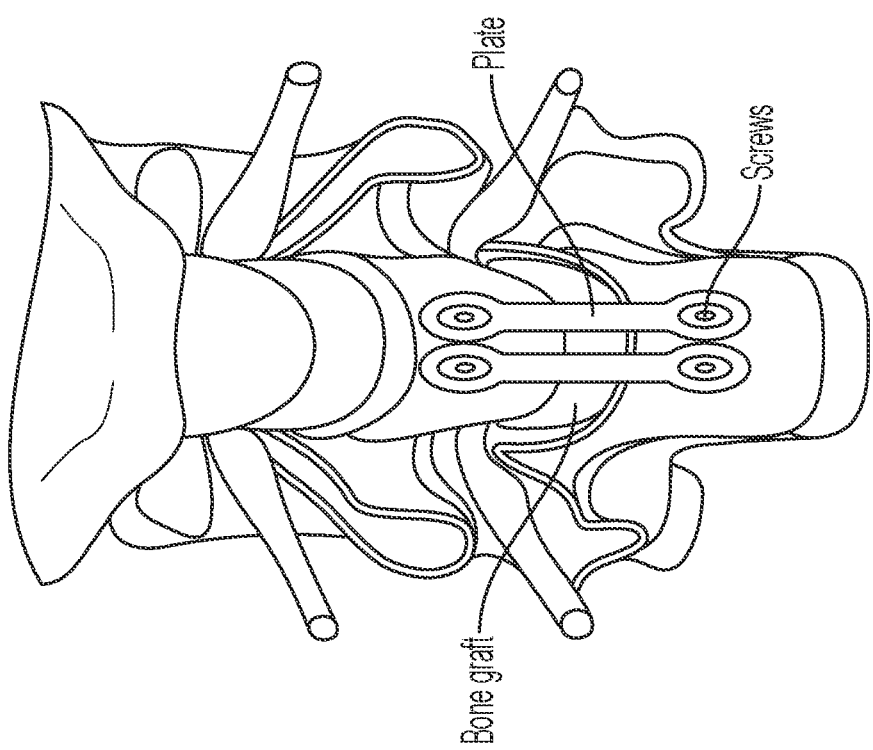
FIG. 5 shows an example of anterior cervical discectomy and fusion.

FIG. 5 shows an example of anterior cervical discectomy and fusion.

Figure 6:
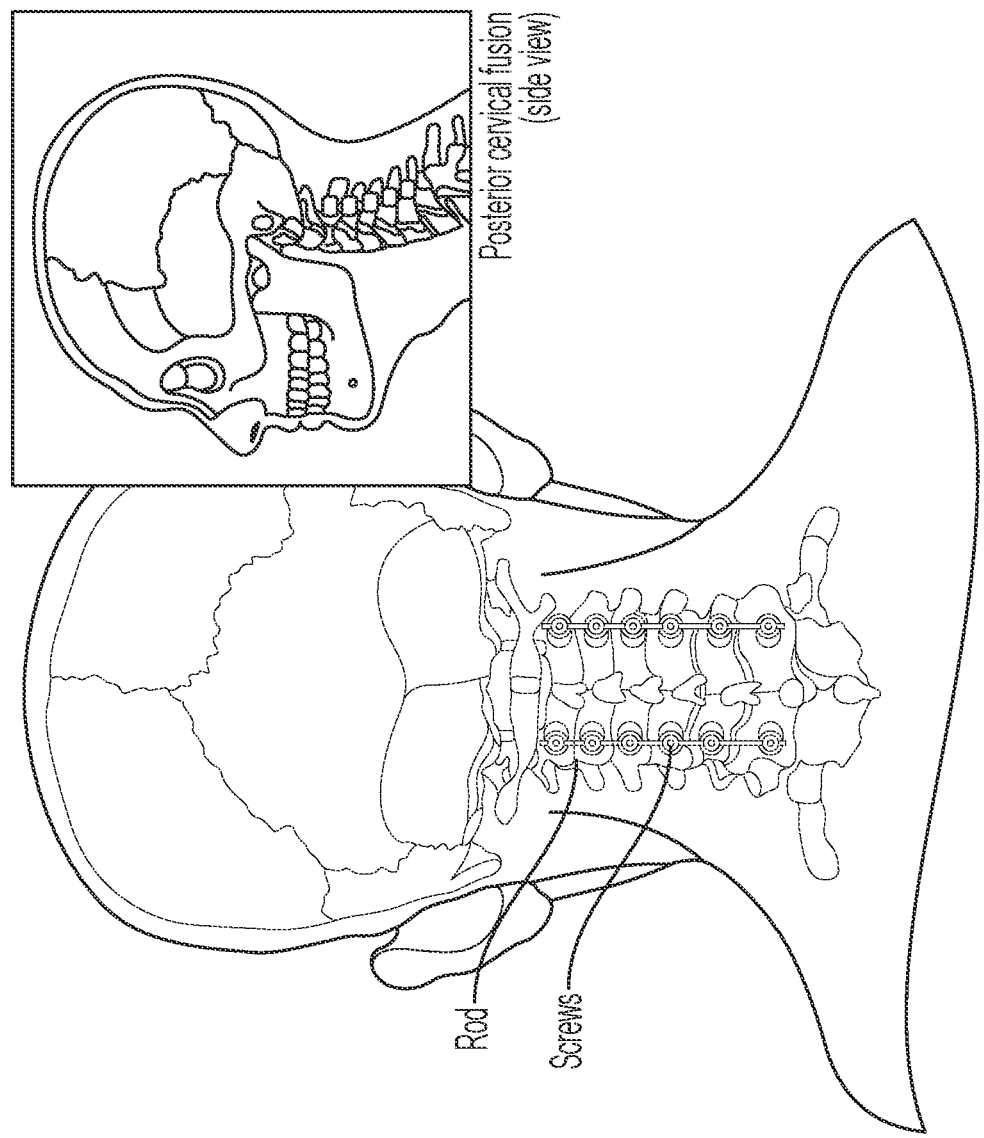
FIG. 6 shows an example posterior cervical fusion.

FIG. 6 shows an example posterior cervical fusion.

Figure 7:
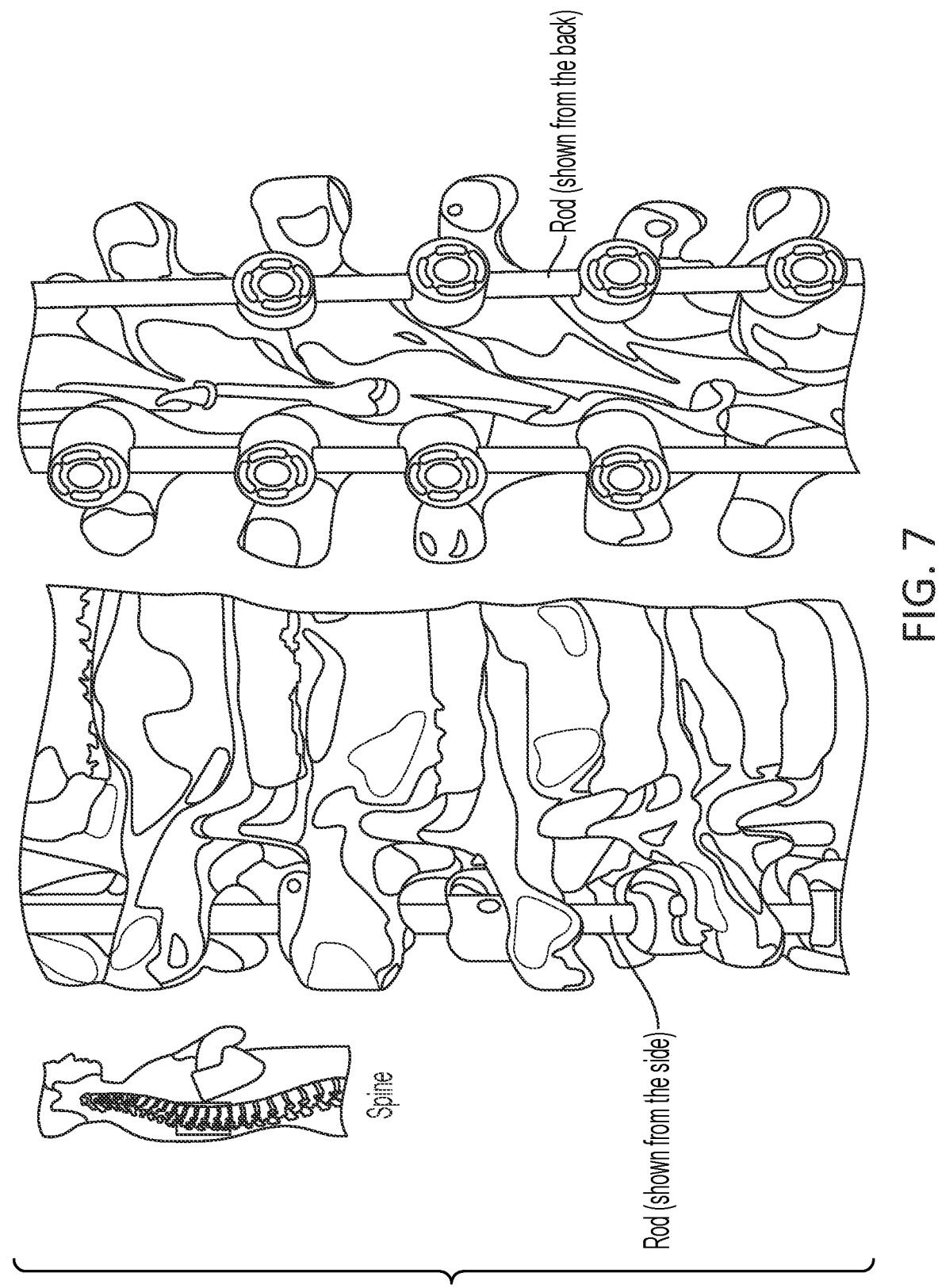
FIG. 7 shows a lateral and posterior view of a multi-level spinal fusion including spinal rods connecting screw sets anchored in the patient vertebrae.

FIG. 7 shows a lateral and posterior view of a multi-level spinal fusion including spinal rods connecting screw sets anchored in the patient vertebrae.

Figure 8:
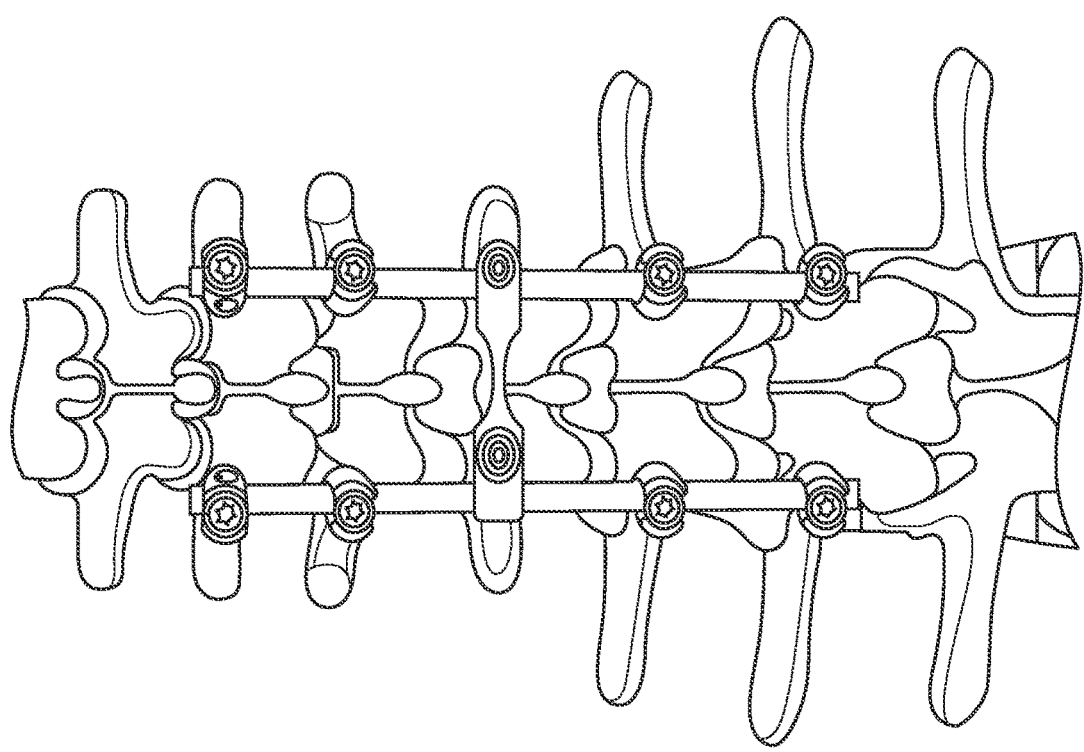
FIG. 8 also shows a posterior view of a multi-level spinal fusion including spinal rods connecting screw sets anchored in the patient vertebrae, and connectors joining left and right rods.

FIG. 8 also shows a posterior view of a multi-level spinal fusion including spinal rods connecting screw sets anchored in the patient vertebrae.

Figure 9:
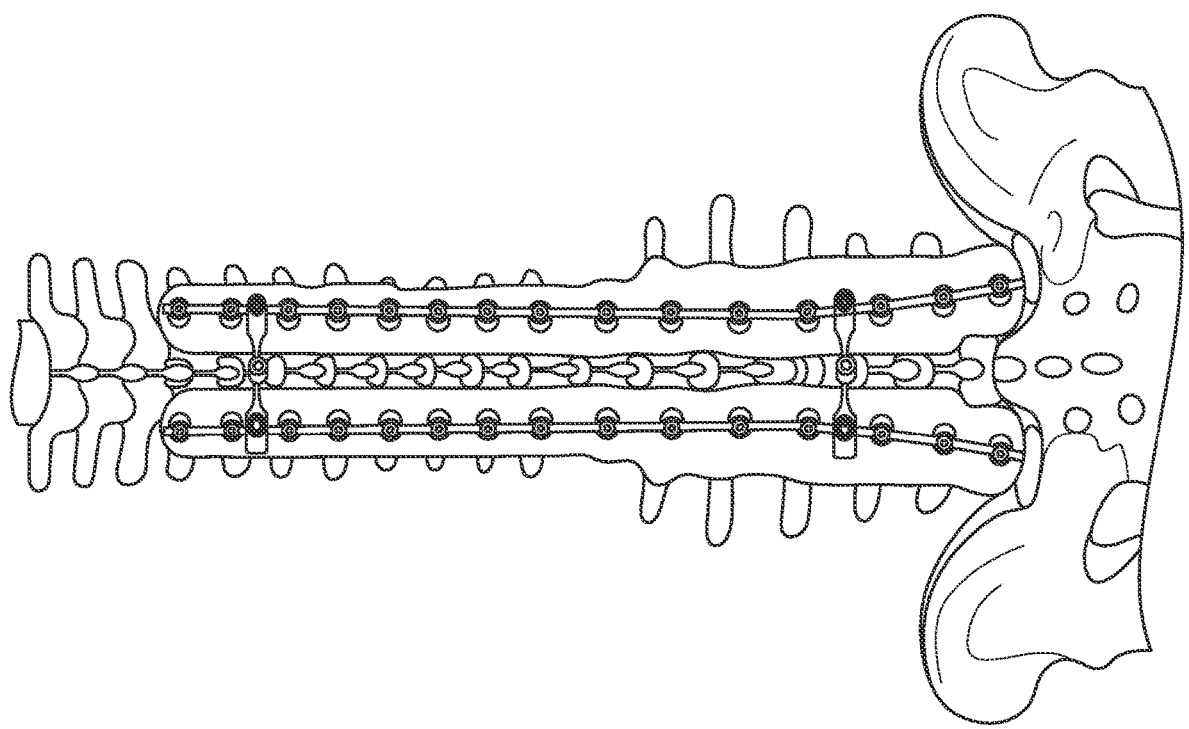
FIG. 9 shows an example spinal system. The system uses a Co-28Cr-8Mo alloy, with typical mechanical properties as shown in the table below.

FIG. 9 shows an example spinal system. The system uses a Co-28Cr-6Mo alloy, with typical mechanical properties as shown in the table below.

FIG. 10 shows a table of mechanical test requirements for Co-28Cr-6Mo alloy as per ASTM F1537.

Elastic Modulus

The elastic modulus for implant cobalt alloys, as well as for stainless steels is about 200 GPa; and, for titanium alloys, about half this level, at about 100 GPa, or even lower for beta titanium alloys. To consider a new, spinal implant alloy that could provide a higher elastic modulus and the associated desirable implant stability, as well as the other desired properties mentioned above, the use and development of refractory metals and their alloys are described, particularly more affordable tungsten and molybdenum.

Refractory metals and their alloys are primarily used for high temperature applications that require high recrystallization temperatures, required for long term resistance to creep and strength degradation. The following tables summarize the various refractory metals and their melting temperatures. For the present technology, high-modulus alloy, the desired elastic modulus is above 300 or about 300 GPa. The desired elastic module is in some cases over about 325 Gpa, and in some over about 350 Gpa.

Figure 11:
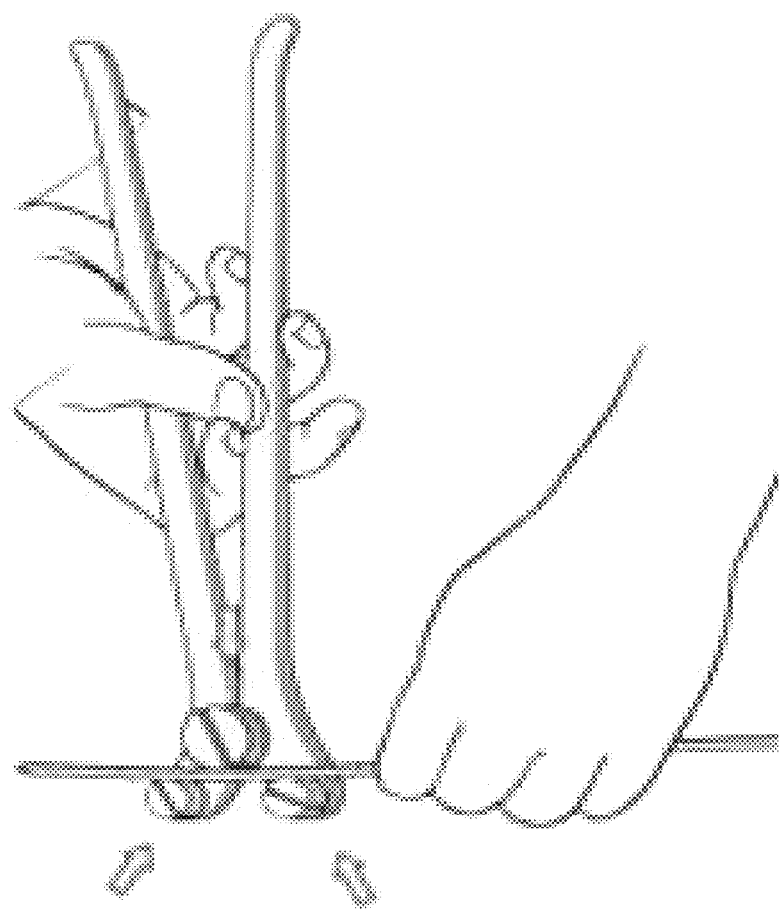
FIG. 11 shows an example manual rod-bending process performed away from the patient.

FIG. 11 shows an example manual rod-bending process performed away from the patient. Rod benders are typically used to apply a desired local bend to a rod as the surgeon advances the rod through the bender, or vice versa.

Figure 12:
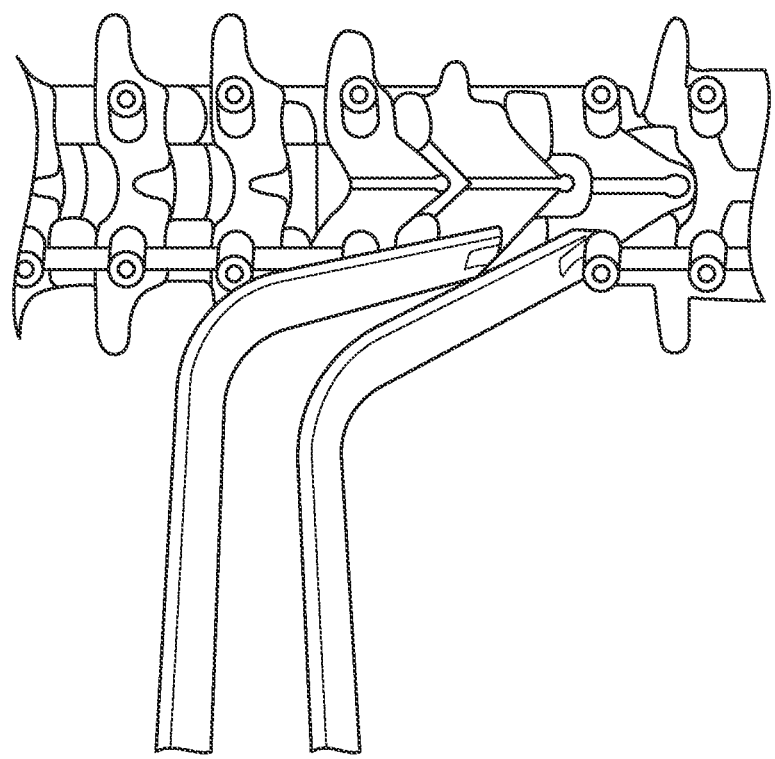
FIG. 12 shows an example manual rod-bending process performed in-situ, with the rods already implanted.

FIG. 12 shows an example manual rod-bending process performed in-situ, with the rods already implanted. Coronal/in-situ benders are used once the rod has been placed in the anatomy, for instance, to fine tune the desired curvature for assembling the construct.

Thus, in some embodiments of the alloy according to the present technology, a high-modulus composition having a high ductility is provided. The addition of small amounts of one or more transition elements such as Hf, Ta, Nb, and the like can improve the ductility (and to some degree, the corrosion resistance) of the alloy according to the present technology.

Figure 13:
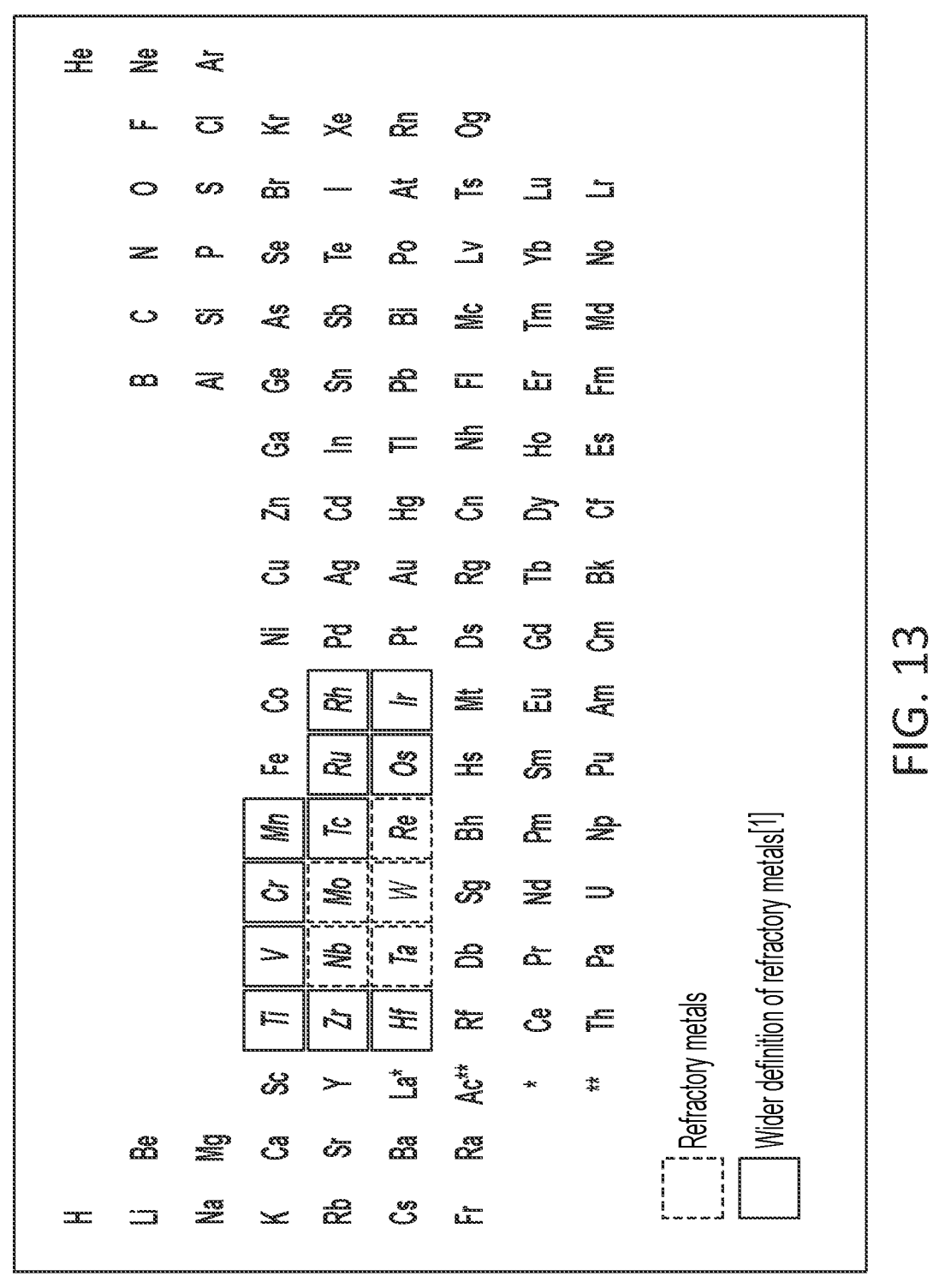

FIG. 13 shows a periodic table highlighting groups referred to as refractory elements. The highlights include (i) a first for refractory materials according to one definition, and (ii) a second for refractory materials according to a wider definition.

The elements of interest are those more common elements, tungsten (W), molybdenum (Mo), and rhenium (Re) with exceptionally high elastic modulus. Others, with lower elastic moduli can also considered as useful for modifying the strength, elongation, and corrosion resistance. These various elements and their properties are summarized in the table below. Note also the levels of magnetic susceptibility which are desirable for imaging. For example, Iron, Nickel, and Cobalt are all ferromagnetic and very magnetic. Due to the high cost of rhenium, it is not a preferred addition to the alloy according to the present technology, and both tungsten and molybdenum are the preferred base metals of the compositions of the present technology.

FIG. 14 is a table showing values for various properties, for select materials. Regarding magnetic susceptibility, it is noted that Co, Ni, Fe are example ferromagnetic materials. Regarding cost/kg, it is noted, by way of example, that iron is about $0.10/Kg, Ti=$5/Kg, Ni=$17/Kg, and Co=$38/kg.

Typical hardness of CoCrMo alloy is about 42-47 Rc, and 316L Stainless steel (cold-worked) is about Rc 20.

Considerations for Development of a High-Modulus Alloy for Implants

Cost Factor

As seen in the table of FIG. 14, the cost of a new, high-stiffness implant alloy will be a major consideration in comparison to relatively low-cost stainless steels. The base metal alloy compositions will need to include the higher-modulus metals such as Mo, and W. Smaller additions of other elements can be considered, but at the expense of the desired high modulus and, hopefully, abrasion resistance. And other elements are included within the scope of this alloy according to the present technology for improved and acceptable corrosion resistance in the aqueous chloride body environment and for increased ductility.

Corrosion

In general, the refractory metals are relatively non-toxic, and summarized below from the refractory metal fact sheet. Of these various metals, rhenium is the least environmentally friendly. This is an additional reason that rhenium is not a preferred alloy addition to the alloy according to the present technology. However, it is still important to add corrosion protection when these metals and alloys are placed into an aqueous chloride environment. Thus, for the alloy according to the present technology, the addition of any one or more of chromium, tantalum, niobium, etc. provides this additional corrosion protection in the body.

FIG. 15 is a table comparing refractory metals in terms of environmental impact. Reference is made here to a publication, Life Cycle Assessment of Metals: A Scientific Synthesys paper, Nuss P & Eckelman MJ, 2014).

As stated in the table of FIG. 15, Rhenium and Tantalum are the most environmentally unfriendly of the refractory metals, with higher potential for contributing to global warming, higher cumulative energy demand, and higher levels of terrestrial acidification. However, potential danger in terms of freshwater eutrophication and human toxicity are relatively low, as these metals are considered to be non-toxic.

Sintered and amorphous molybdenum alloys containing significant amounts of tantalum, titanium, chromium and niobium have all been found to offer excellent resistance to strong reducing acids such as hot concentrated hydrochloric, sulfuric, phosphoric, oxalic and formic. For example, a sintered Ti-40Mo alloy corrodes between 1000 and 10 000 times more slowly than Ti in boiling 35% hydrochloric acid although the corrosion rate in neutral conditions was unaffected.[24] Likewise, binary amorphous Mo—Cr, Mo—Nb, and Mo—Ta alloys all show spontaneous passivity in 12 M HCl with overall corrosion rates, in all cases, significantly less than the individual alloy components (Shreir's Corrosion Volume 3, 2010, Pages 2157-2167).

As mentioned earlier, the chloride corrosion resistance of current implant metals, such as 316 and 304 stainless steels and Cobalt-Chrome-Molybdenum alloys is derived from the addition of chromium in amounts exceeding about 18 weight percent. The presence of the chromium creates corrosion protection due to the formation of a thin, passive, protective chromium oxide layer. Titanium, Niobium, Tantalum, Hafnium, and Zirconium alloys naturally form their own highly-protective passive surface oxides that render these metals highly resistant to chloride corrosion, but can be alloy additions in the invention alloy to assist with the ability of the invention alloy to self passivate.

Essentially the refractory metals and alloys are more corrosion resistant than iron and cobalt, including tungsten, rhenium, and molybdenum. However, additional corrosion protection in aqueous chloride environments is required for these base metals to have comparable corrosions resistance as current implant alloys. High-modulus molybdenum or tungsten alloyed with, for example, chromium, can be expected to have sufficient corrosion resistance, similar to that of stainless steels (alloyed with a minimum of about 12-18% Cr).

The presence of both Mo and Cr in the same alloy has been noticed to have a synergistic effect as the alloy performs better compared to the ones that lack either element.

The benefit of alloying Mo could be just to support and complement Cr; therefore, the advantageous effect of Mo is mostly not as pronounced as Cr. The good compatibility between Cr and Mo could be due to their identical structure which is body centered cubic and similar lattice parameters.

Similar to CrMo, MoW is also said to have a synergistic effect. Mo and W behave very similar in terms of preventing pitting or crevice attack. The two elements in combination with chromium have been noted to provide passivity by promoting the growth of a chromium-rich inner layer. The presence of small levels of yttrium can additionally improve the ability of the chromium to form a protective corrosion-resistant passive surface oxide. In terms of structure, both Mo and W are very much alike. Both are considered as refractory elements due to their high melting temperatures, and both have body centered cubic structures.

Consideration is also given to how W and Cr would interact in the absence of Mo. Whether W could complement Cr as well as Mo is another compelling consideration. It appears that Mo not only functions to provide corrosion protection by its own virtue but also to strengthen the protection given by other elements. There are thus synergistic reactions providing known and further potential benefits.

Alternatively, these refractory metals and alloys may be able to improve corrosion resistance by the addition of niobium, tantalum, zirconium, titanium, and hafnium.

Mechanical Properties

Figure 16:
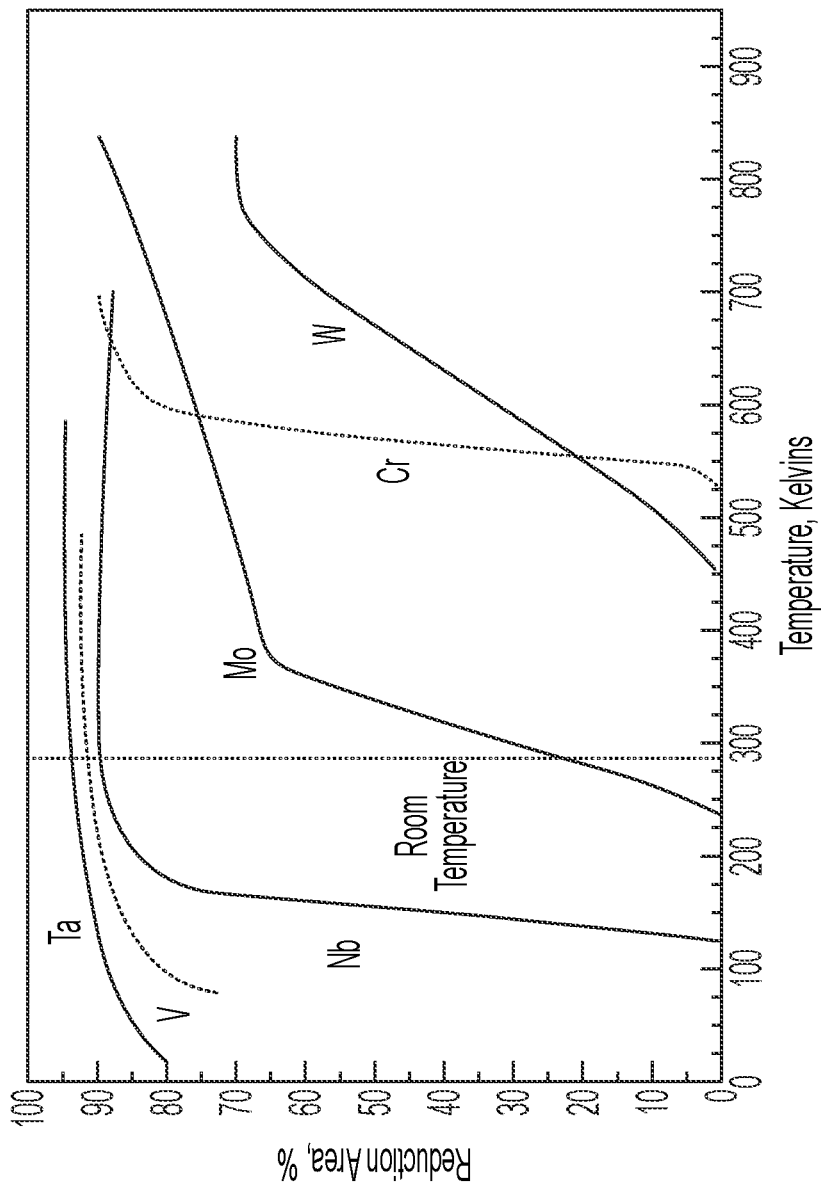
FIG. 16 is a chart showing ductile-to-brittle transition behavior of refractory metal versus temperature.

In the alloy according to the present technology, it is desirable to have an alloy that is not brittle. FIG. 16 shows the brittle behavior of chromium and tungsten, and to a lesser degree, molybdenum at body temperature (about 310 Kelvin). The chart shows, particularly, ductile-to-brittle transition behavior of refractory metal versus temperature.

When tungsten is alloyed with molybdenum, though, there can exist a ductile, non-brittle, alloy. Further, in appropriate proportions, the hardness (strength) and, thus, ductility can be varied for the desired medical device application. In part, this is because molybdenum and tungsten are fully miscible with each other (see the Mo—W phase diagram). As the amount of each varies, the alloy hardness varies as shown below (related to strength and ductility). Thermo-mechanical processing of the lower-hardness casting increases the homogeneity of the alloy and associated hardness (and strength).

Figure 17:
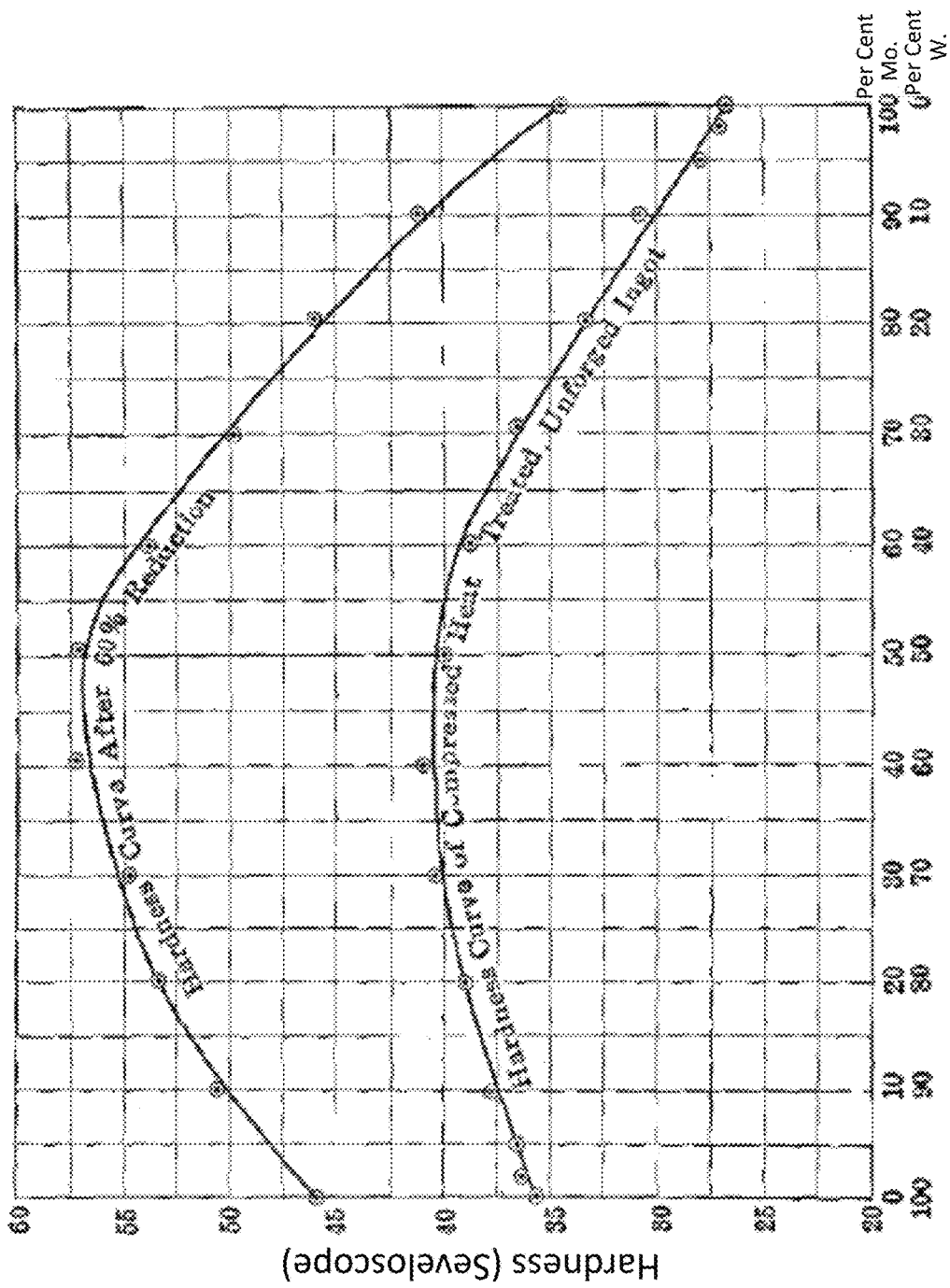
FIG. 17 is a chart showing two hardness curves.

FIG. 17 is a chart showing two hardness curves for various compositions of Mo and W. Hardness is related to strength and ductility, thus, by varying this base composition, the optimum combination for high strength and ductility can be obtained and which can include the other required elements for self-passivation in an aqueous chloride environment.

As the considerations for this new, high-modulus implant alloy consider new elemental compositions, there is very limited information regarding the effect of a particular element on the mechanical properties of tungsten, molybdenum (and rhenium). There are, however some selected information and trends that can be considered in developing the likely composition of this alloy according to the present technology. The relationship (general trend) between hardness and tensile strength of metals can help estimate the strength and ductility of the candidate high-modulus alloys. For example, increased molybdenum should reduce strength and increase ductility. On the other hand, increased tungsten should increase strength, likely at the expense of ductility.

Figure 18:
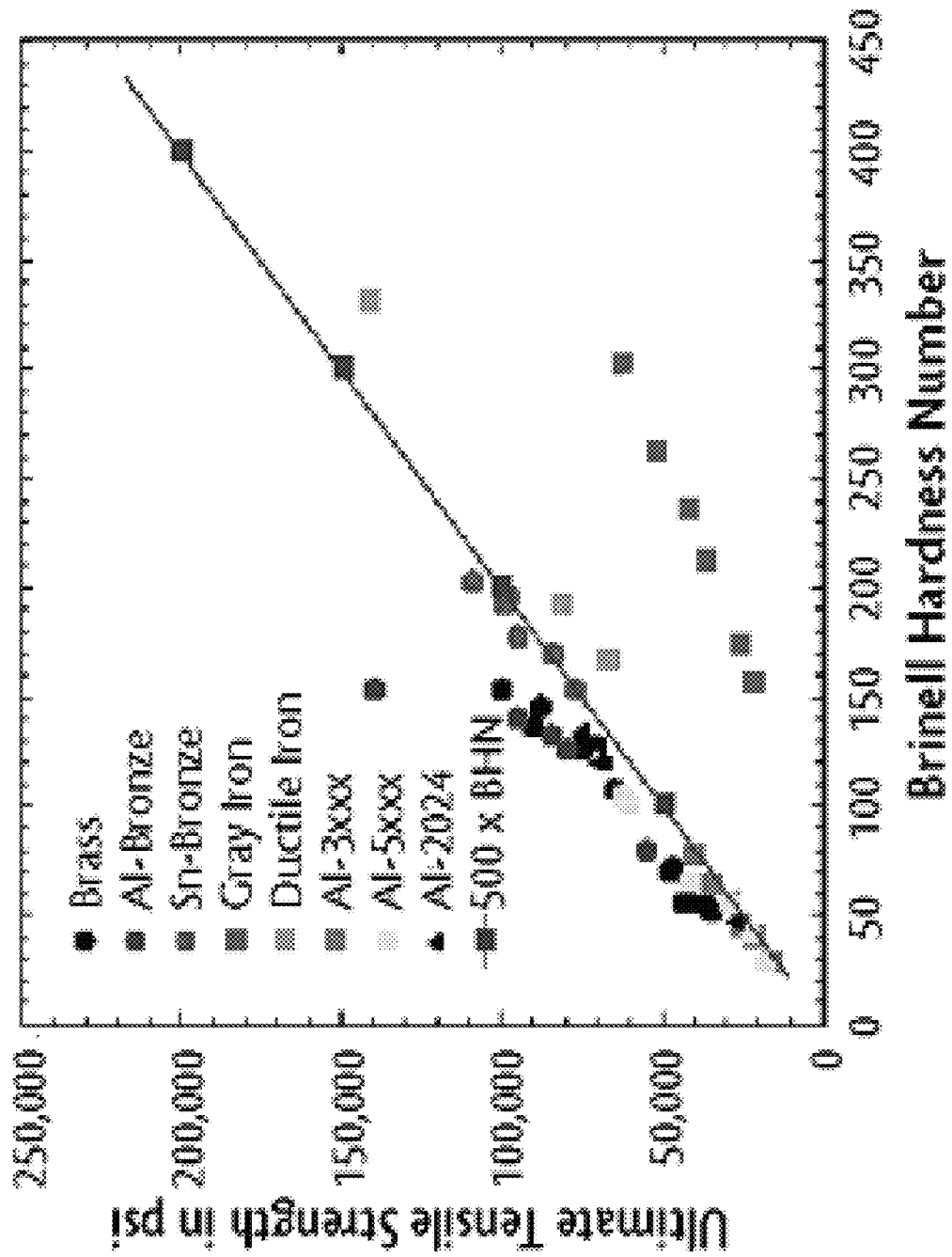
FIG. 18 is a chart showing a compilation of ultimate tensile strength versus Brinell hardness for selected metals.

FIG. 18 is a chart showing a compilation of ultimate tensile strength versus Brinell hardness for selected metals.

Minimizing/Eliminating Rhenium

A first consideration is the desire for an alloy having a relatively high elastic modulus. The main alloy composition in various embodiments thus needs to contain a suitable combination of tungsten and molybdenum (and/or rhenium). But for cost and potential toxicity/corrosion reasons, it is desired to minimize or eliminate the amount of rhenium. If rhenium is considered as part of the alloy according to the present technology, though, (and, if so, primarily only with tungsten in select embodiments), then it is important to realize that the addition of rhenium can further provide alloy options with improved ductility at body temperature as shown in the figure below.

Generally, a sufficient amount of ductility is for various embodiments required for the doctor to plastically deform the spinal rod, for example, during surgery. But this requirement is primarily for spinal rod applications, and less important for plates, anchors, fusion devices, screws and other implant devices.

Figure 19:
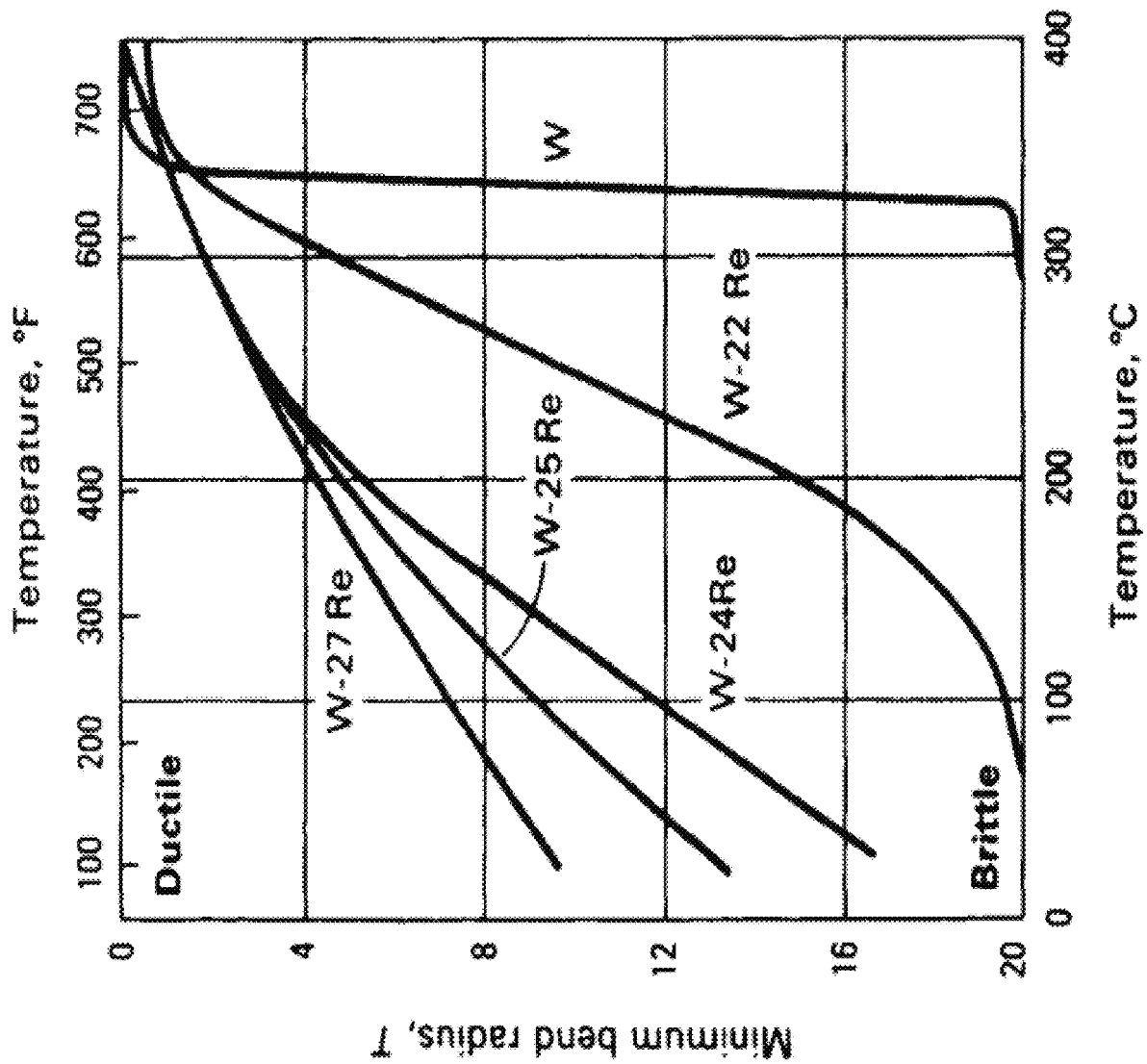
FIG. 19 is a chart showing effect of alloying additions of rhenium on ductility.

FIG. 19 shows the effect of rhenium on the ductility of tungsten. The figure is a chart showing effect of alloying additions of rhenium on ductility. An amount of rhenium in excess of about 25% is required to provide sufficient ductility at body temperature. Thus, the presence of rhenium in such quantities is undesirable in most or all embodiments.

For spinal and implant devices other than rods, less ductility can be accepted. Again, sample "button" melts of various elemental combination will be required to assess the most desirable alloys or alloy combinations according to the present technology.

A factor in creating candidate alloy compositions in some embodiments will be related to their metallurgical phase diagrams. These diagrams describe the ability of one element to melt and form a stable, equilibrium, single-phase alloy with another element upon cooling. These examples include Mo—W, Mo—Nb, Ta—W, and Mo—Ta. If two elements are immiscible, this may be undesirable, as phase separation can create uneven distribution of the elements and potentially, brittle inter-metallic compounds.

On the other hand, if two or more elements appear to be highly miscible, then this is a positive indication that the new alloy can be uniform and metallurgically acceptable. And when assessing the various phase diagrams, it is important to factor in other elements (Cr, Nb, Ta, Hf, etc.) that can serve to improve the corrosion resistance of the final alloy in aqueous chloride environments, and other beneficial mechanical characteristics.

Small amounts of Hafnium can soften the alloy, for instance. And 1-3% niobium in Mo increases tensile elongation (ductility). This further substantiates the need for no expensive rhenium in the alloy according to the present technology. Even Mo-30% W shows a strength of about 685 MPa and elongation of about 20% in the stress relieved condition. So, perhaps a 50Mo-35W-10-15% Cr alloy may be acceptable. Or add tantalum and/or niobium in lieu of the chromium or tungsten, and so forth.

Phase Diagrams and Potential Alloy Compositions

Following are various phase diagrams showing the miscibility of various elemental compositions.

Figure 20:
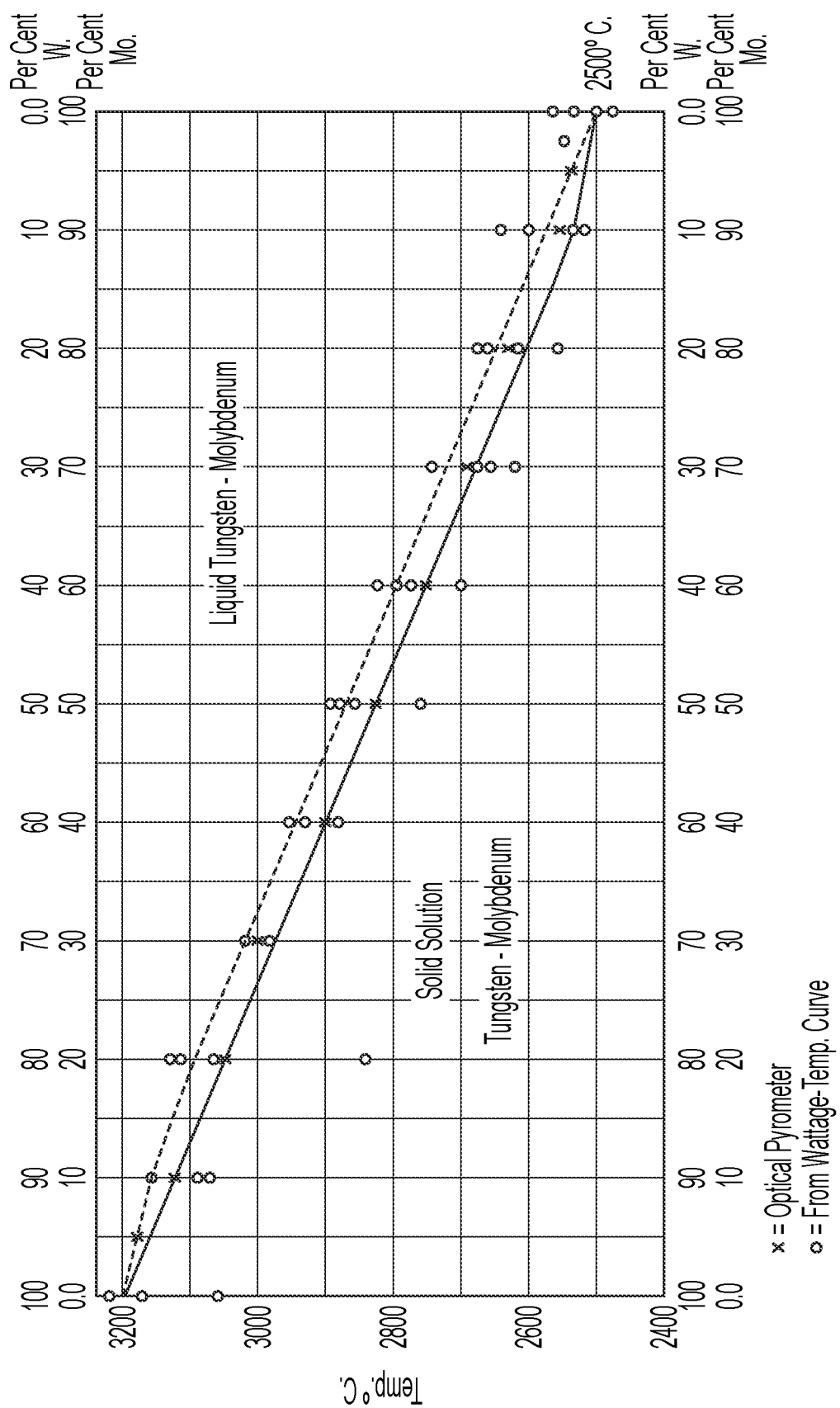
FIG. 20 shows a phase diagram for Tungsten-Molybdenum.

FIG. 20 shows a phase diagram for Tungsten-Molybdenum.

Figure 21:
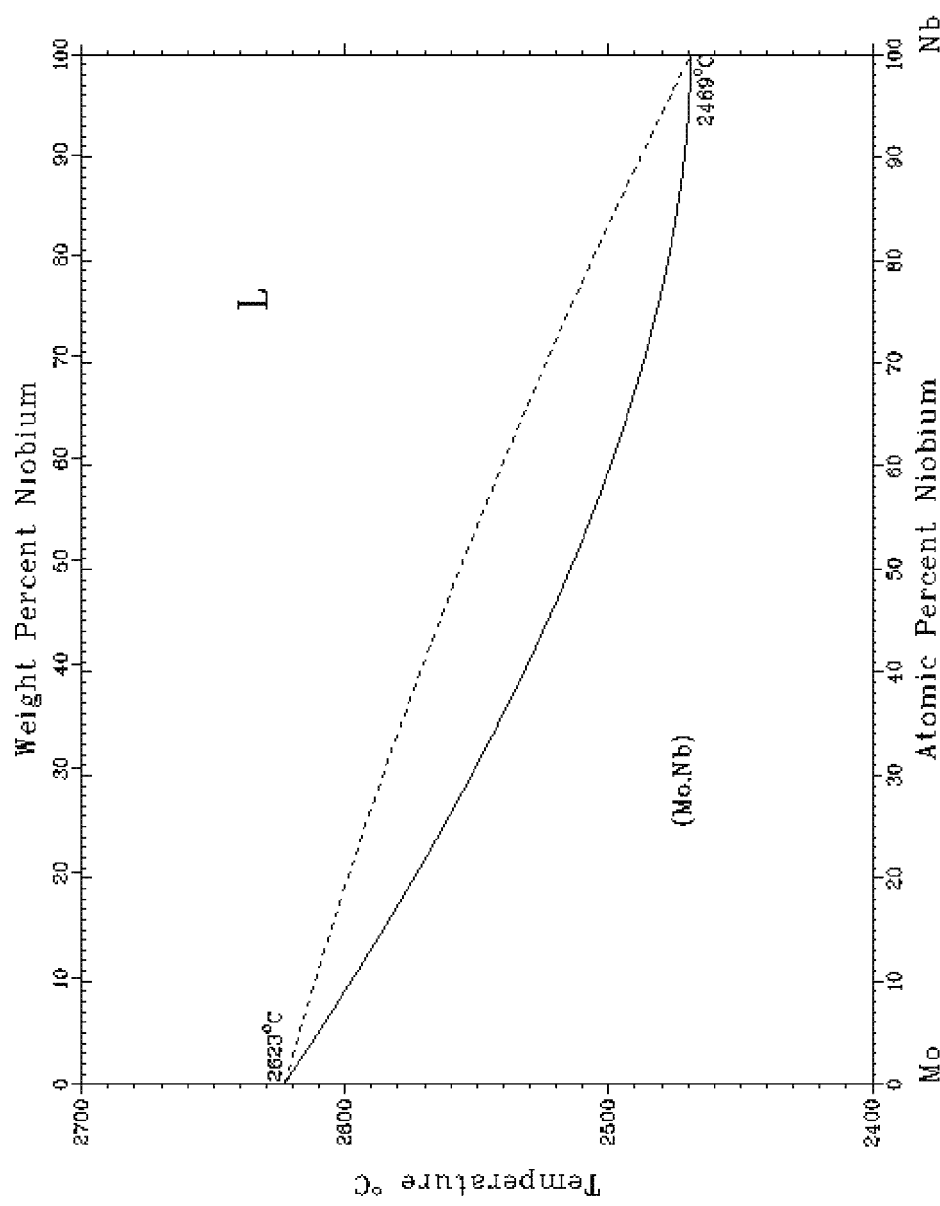
FIG. 21 shows a phase diagram for Molybdenum-Niobium.

FIG. 21 shows a phase diagram for Molybdenum-Niobium.

Figure 22:
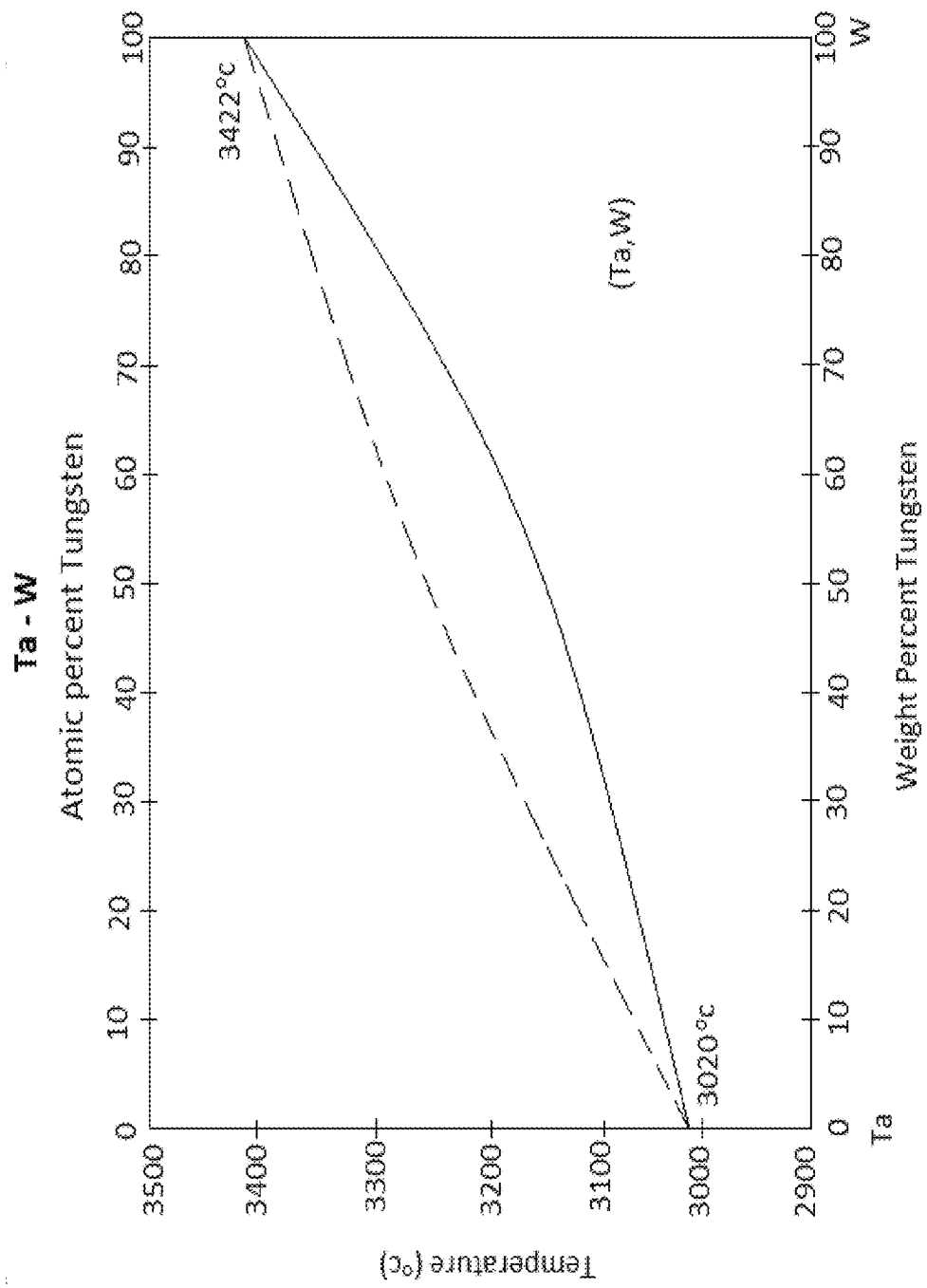
FIG. 22 shows a phase diagram for Tungsten-Tantalum.

FIG. 22 shows a phase diagram for Tungsten-Tantalum.

Figure 23:
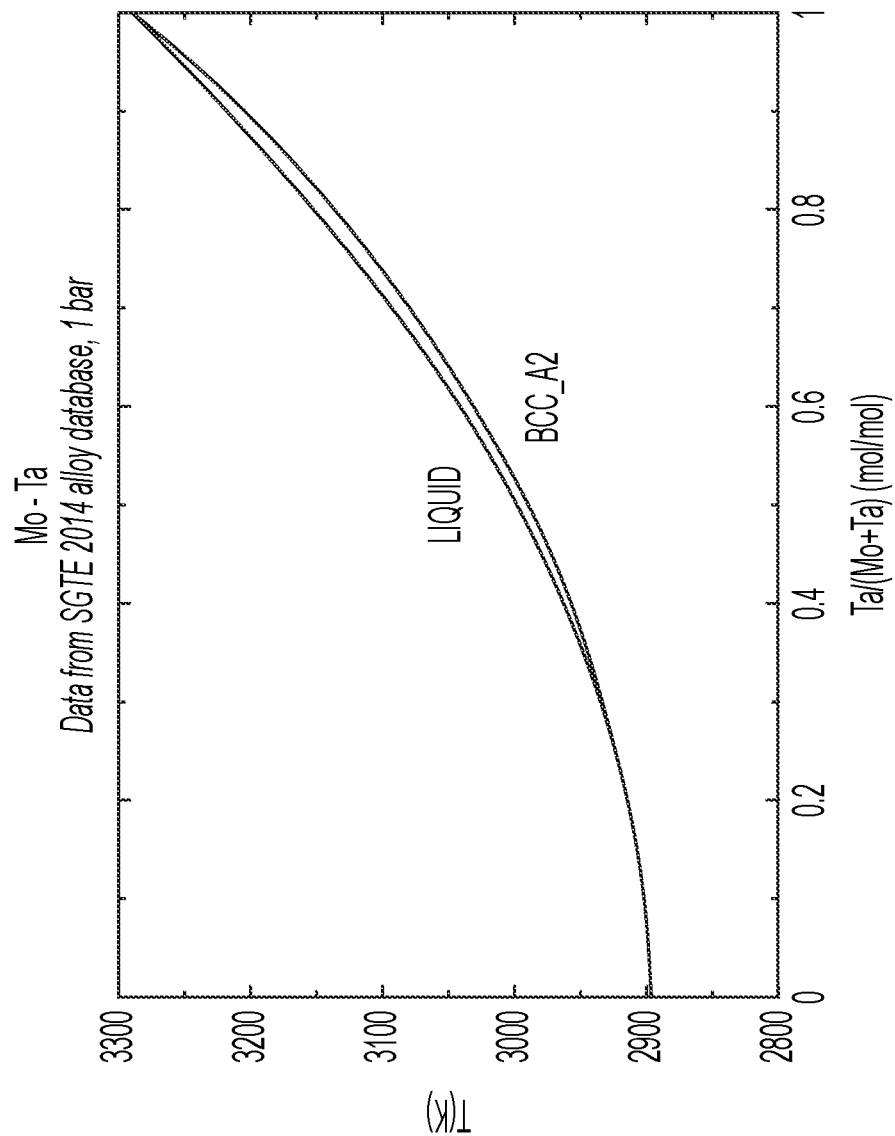
FIG. 23 shows a phase diagram for Molybdenum-Tantalum.

FIG. 23 shows a phase diagram for Molybdenum-Tantalum.

Figure 24:
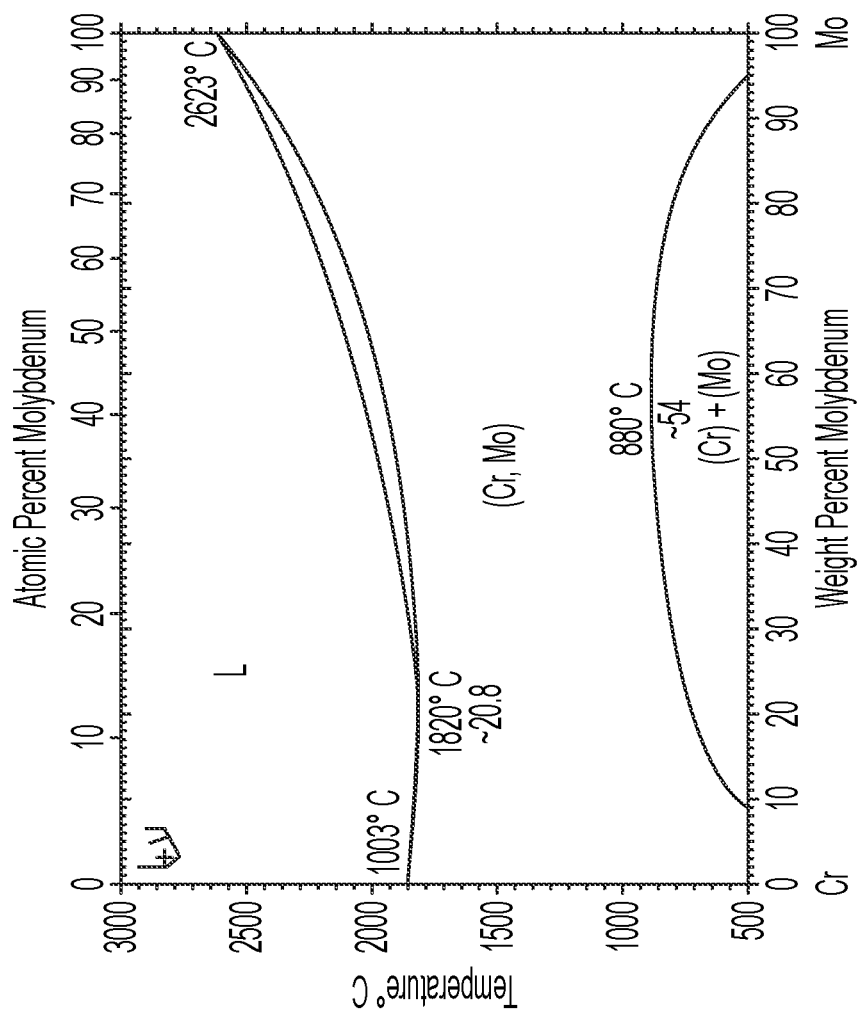
FIG. 24 is a phase diagram for Molybdenum-Chromium.

FIG. 24 is a phase diagram for Molybdenum-Chromium (Mo—Cr).

Figure 25:
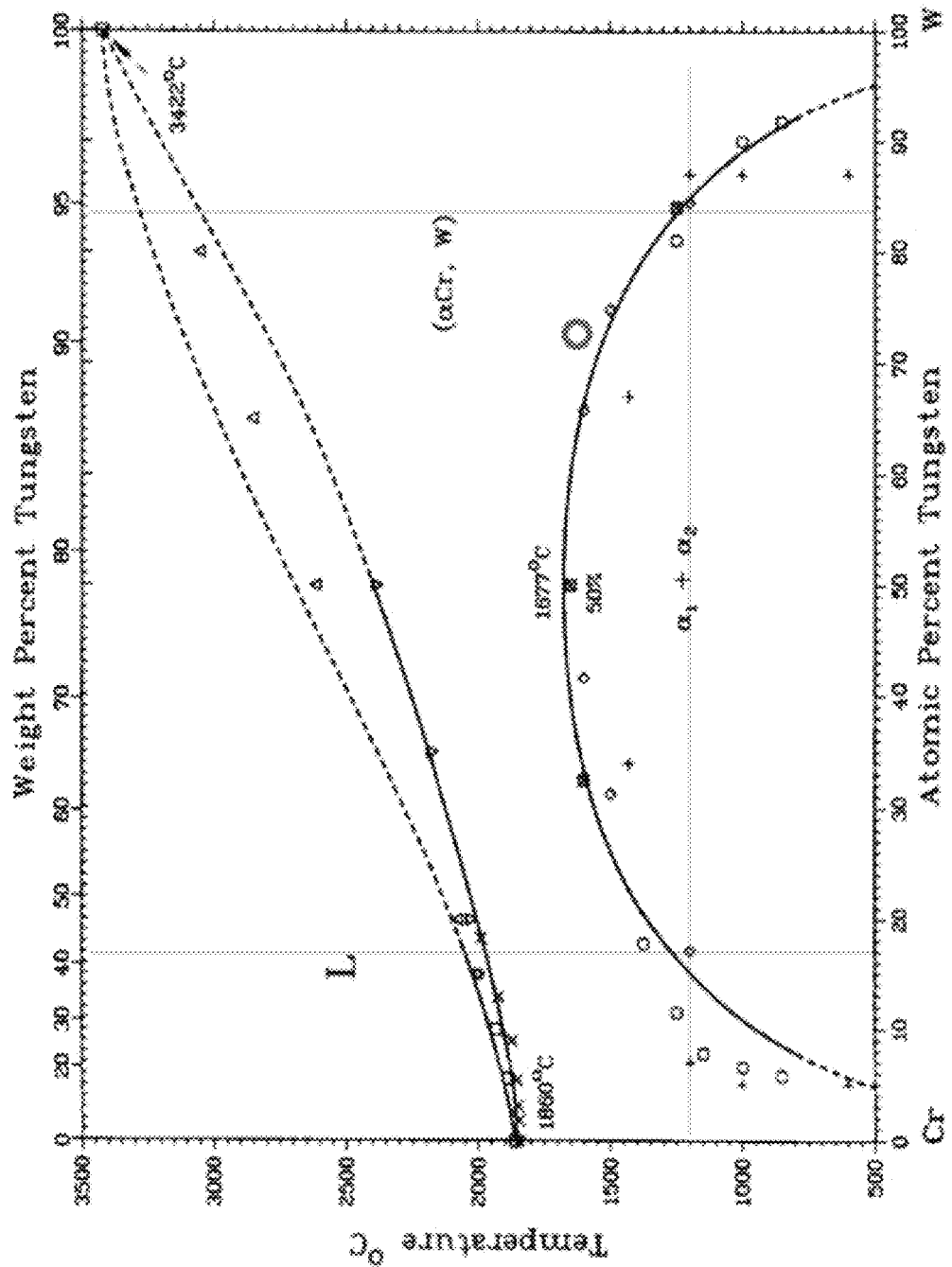
FIG. 25 shows a phase diagram for Tungsten-Chromium.

FIG. 25 shows a phase diagram for Tungsten-Chromium.

Figure 26:
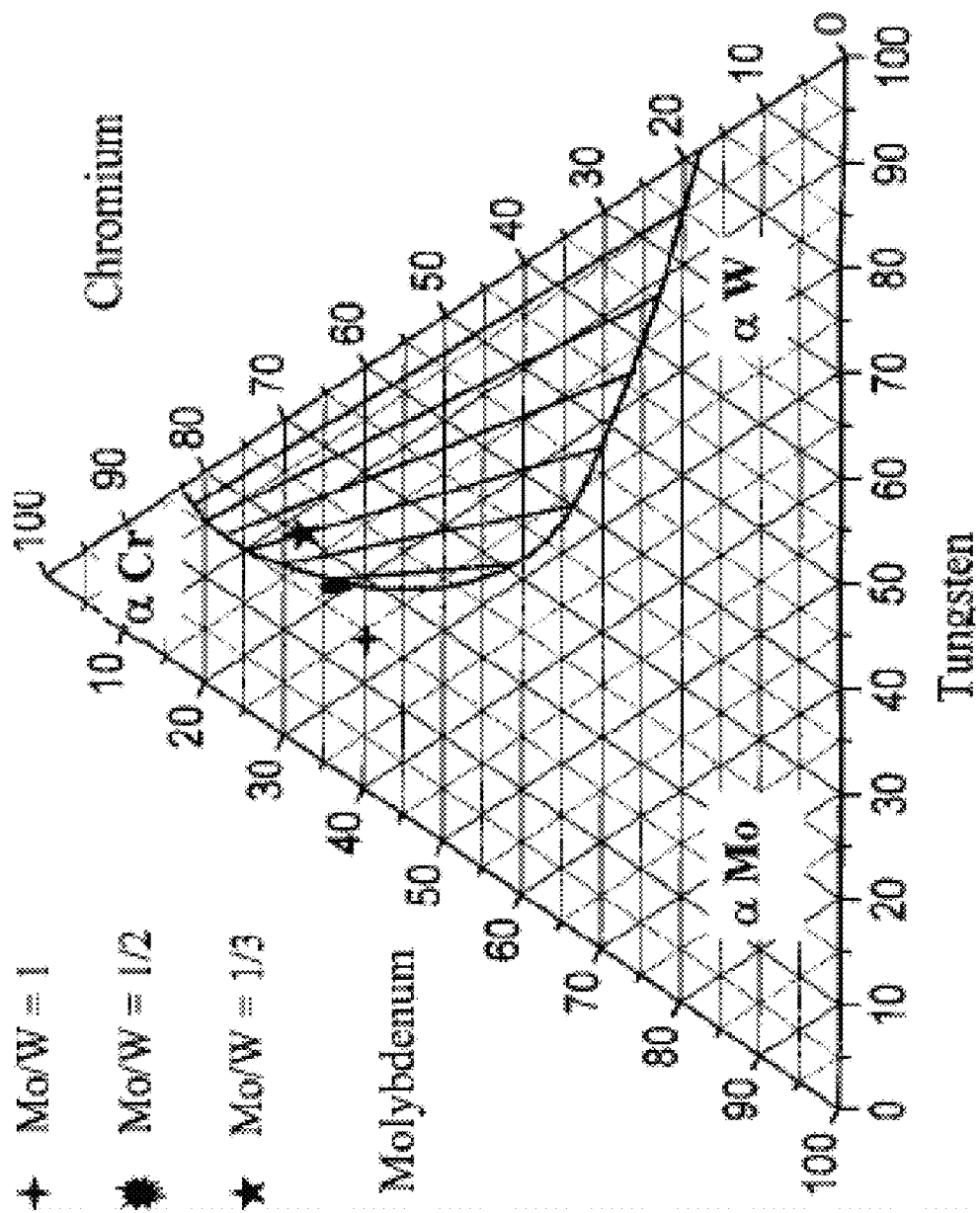
FIG. 26 is a phase diagram for Tungsten-Molybdenum-Chromium ternary.

FIG. 26 is a phase diagram for Tungsten-Molybdenum-Chromium ternary,

Observations from the Various Phase Diagrams

W—Nb, W—Mo, W—Ta, and Mo—Nb: Fully miscible.

Mo—Cr and W—Cr: miscibility gap ABOVE about 4 wt. % Cr. But, in combination with Mo and W, then this expands.

Rhenium: Each of Mo—Re, W—Re, Ta—Re, Nb—Re, and Cr—Re is not fully miscible and form many additional phases which affect homogeneity. This can be an additional reason to avoid or eliminate Rhenium in the alloy composition according to the present technology.

Compositional Considerations for the Alloy According to the Present Technology

Based on the above metallurgical phase diagrams, about a 50Mo-30-40% W- and 10-20% Cr alloy should be a good candidate alloy composition. As another example, any of the alloys shown in FIG. 27 can be included, such as 40Mo50W10Cr.

It would be useful to assess this alloy with 3%, 6% 10% and 15% Cr to determine the level of chromium for optimal or sufficient passivation in an aqueous chloride environment. And w/wo Nb (3-5% is considered a possibility, but just one example range). Or increased W for increased strength and hardness. And with small additions (<5%) of hafnium and niobium to increase ductility.

Tertiary W—Mo—Cr can be beneficial for having good miscibility for most compositions with low Cr.

Mo—Re, W—Re, and Re—Cr: Typical multiple phases. Phase separation of Cr occurs in Re (may be able to quench through). Moderate levels of Nb in Mo should be acceptable and may provide passivation protection and ductility in lieu of chromium. And smaller levels of Ta in Mo should also be acceptable and provide improved passivation.

Another example of Mo—W—Re alloys is a Mo-13% Re-10% W. The UTS is 1000 MPa, the YS is about 900 MPa, and the percent elongation is about 16% The addition of tungsten in a molybdenum-10% Re alloy increases the strength without deteriorating the ductility. It thus seems that less rhenium may be required to improve ductility if alloyed with both tungsten and molybdenum. However, rhenium is much more expensive and not within the scope of the alloy according to the present technology. The addition of chromium, in combination with niobium, hafnium, and tantalum may suffice as a lower-cost replacement for rhenium.

Regarding the fourth listed item in FIG. 27 (4), the composition confirms that increased tungsten will increase strength, but could be too brittle.

The fifth item shows addition of less tungsten to see if ductility is increased and strength decreased. Can also or instead add 10% Cr to see if that is sufficient to induce self-passivation for the case of more Mo and Less Mo. The inherent corrosion resistance of Mo and W may allow for lower Cr requirement.

The sixth item shows that can add 20% Cr to see if this amount is needed to create self-passivation.

The seventh item shows that can add Ta to see if Cr is not required, and if Ta can increase ductility.

The eighth item shows that can add 5% Ta to see if less Ta can provide corrosion resistance and increased ductility.

The ninth item shows that can the elements of ref. (7) and (8), but to assess the potential benefit of Nb.

The tenth item also shows that can the elements of ref. (7) and (8), but to assess the potential benefit of Nb.

The eleventh and twelfth items were tested to assess the benefit of Cr+Nb for self-passivation and mechanical properties. In some embodiments, Cr is minimized, because there is a miscibility gap in the Mo—W—Cr tertiary phase diagram, so that the alloy is not within the miscibility gap.

Example Candidate New Alloys

Ductility and strength are two variables that can be considered in designing or selecting an alloy under the present technology. More ductility is in some embodiments achieved by inclusion of more ductile materials, such as any one or more of Mo, Nb, Ta, Hf. Inclusion of less ductile materials, such as Cr, or W, can be expected to lower ductility, but add strength and hardness. Thermo-mechanical processing can also alter the level of strength and ductility, where, for Mo—W alloys, stress-relieved properties and stronger than recrystallized alloy.

FIG. 27 is a table showing properties for various materials. It is noted that the value for Est. UTS (MPa), shown in the fourth column of the table of FIG. 27, can increase from hot-working.

As mentioned above, thermo-mechanical processing can further modify/improve the overall combination of the properties for the alloy according to the present technology. As another example, Mo—W alloys, 50-60% Hot-work increases the strength and hardness (10-15Rc) versus Heat treated ingot.

The materials can, optionally, include any one or combination of additions, at any desired level, such as of Nb (Niobium), Ta (Tantalum), Hafnium (Hf), Titanium (Ti), Zirconium (Zr), which can additionally alter the mechanical properties as well as the ability of self-passivation of the invention alloys, etc.

In various embodiments, any or all levels of C, N, H, O, if present, are minimized, or kept as low as possible while still maintaining the desired benefit from its/their inclusion.

Reference is made again, here, to various material cost estimates: Fe=$0.10, Ti=$5, Ni=$17, and Co=$38/kg.

Although Rhenium can add ductility to the W—Mo alloy system, the cost and corrosion resistance of this metal will be a trade-off with the properties desired. Although Re is included in the candidate alloy compositions, it is expected that the addition of minimal Re can provide sufficient ductility, or may even be substituted for less-expensive Ta, Nb, Zr, or Hf as preferred in the invention alloy. It is noted that there may be many alternative implant device applications that will not require the 10 to 15 percent ductility desired for the surgical bending of spinal rods. Thus alternative combinations of strength and ductility are within the scope of the present technology.

The melting, processing, mechanical testing, metallography, and corrosion testing of the above candidate alloys will allow for more refined compositional decisions to be made. Additionally, the alloys according to the present technology will not be ferromagnetic (as are stainless steels, cobalt-chrome alloys, and Nitinol), and should have acceptable corrosion resistance in an aqueous chloride environment.

MRI Compatibility

FIG. 28 is a table showing values for magnetic susceptibility (X10^−6 ppm) for elemental options for alloys of the present disclosure, for various embodiments.

Figure 29:
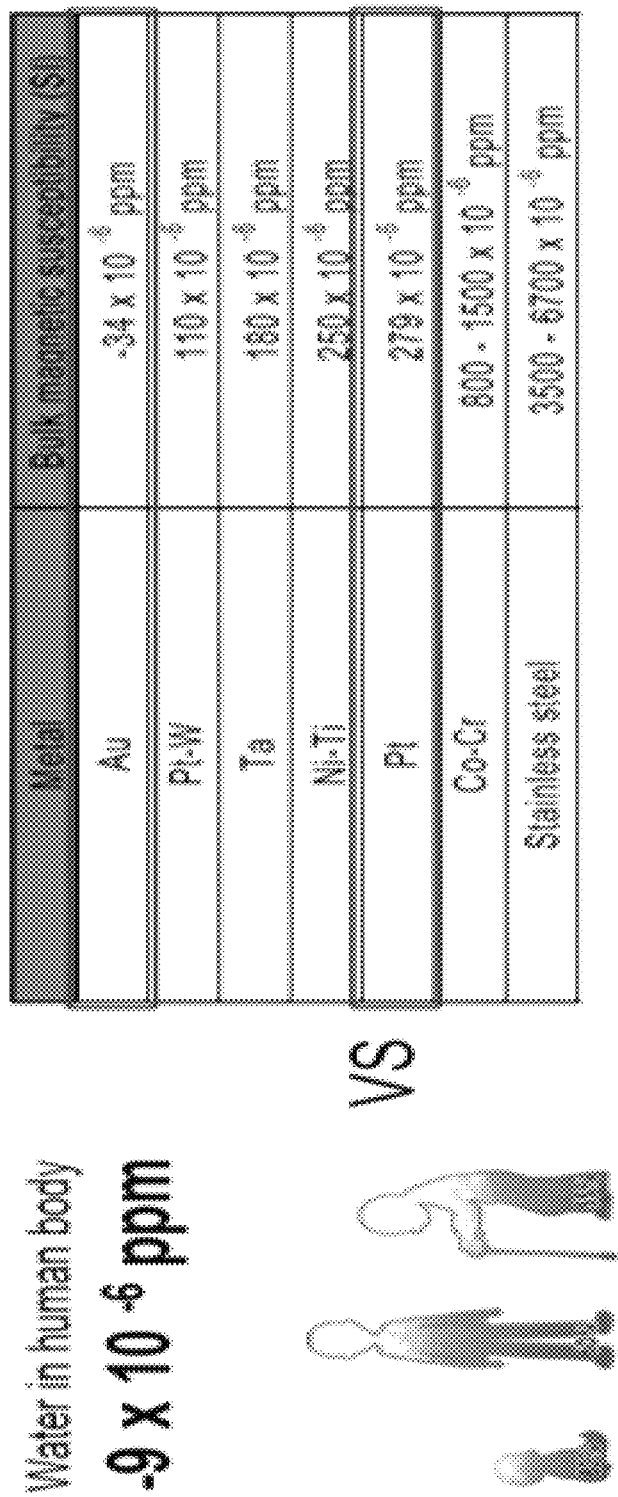
FIG. 29 is a table summarizing levels of magnetic susceptibility for selected implant metals and alloys.

FIG. 29 is a table summarizing levels of magnetic susceptibility for selected implant metals and alloys. To minimize MRI artifact, it is desirable to have the magnetic susceptibility as close as possible to that of water/tissue in the human body ($-9\times10^{-6}$ ppm).

Because molybdenum has a negative magnetic susceptibility and tungsten is positive (more so than rhenium) then the alloy according to the present technology, e.g., Mo—W alloy, options should have favorable magnetic susceptibility compared to, for example, current stainless steels, Nitinol, and Co—Cr alloys. For example, by the rule of mixtures, a 50Mo-40W-10Cr alloy would have an estimated magnetic susceptibility of about $-7\times10^{-6}$ ppm. This is essentially the same as that of the tissue within the human body.

Contextual Information—Example Hardness Relationships

Figure 30:
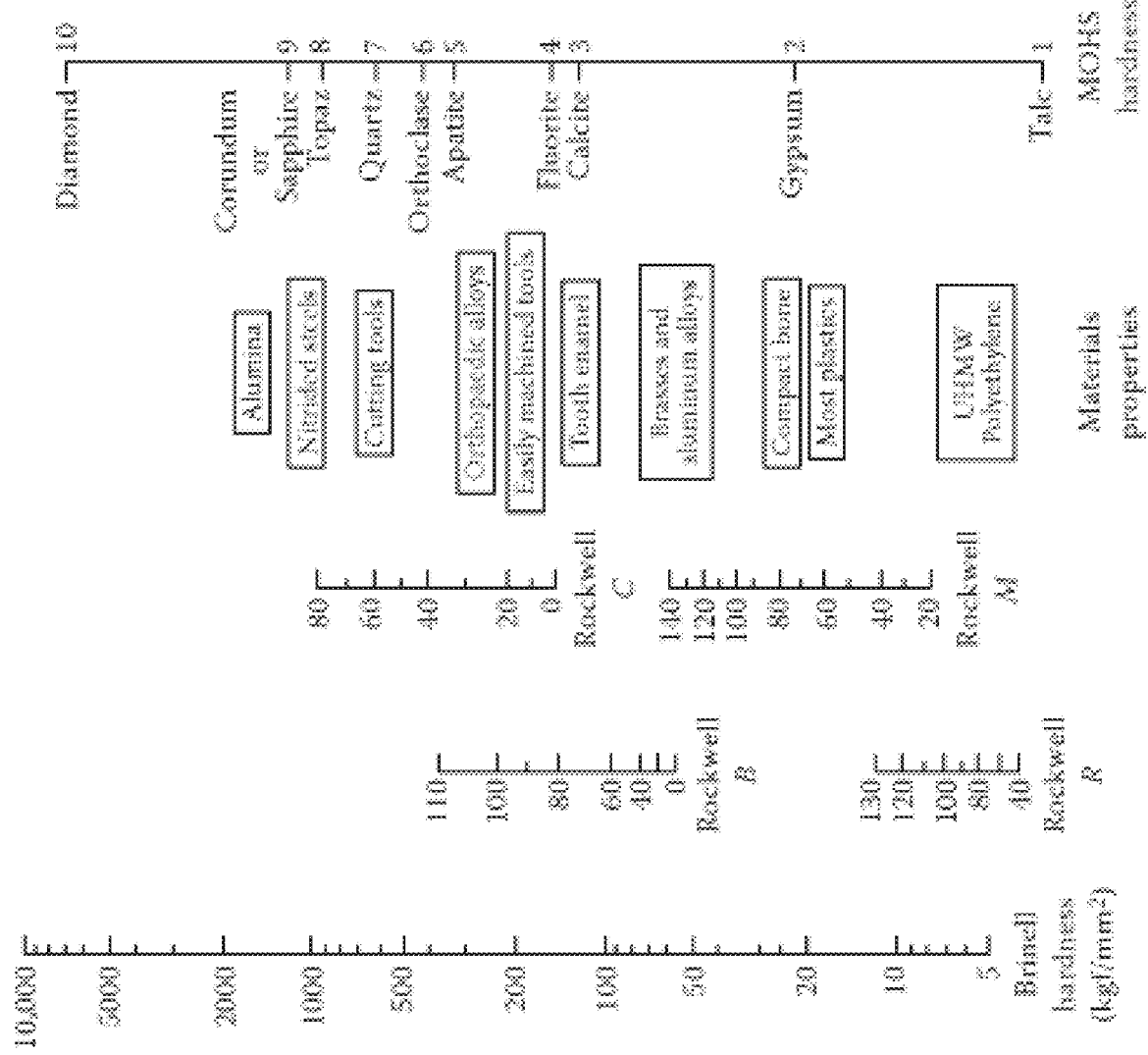
FIG. 30 shows hardness values for various materials.

FIG. 30 shows hardness values for various materials.

Figure 31:
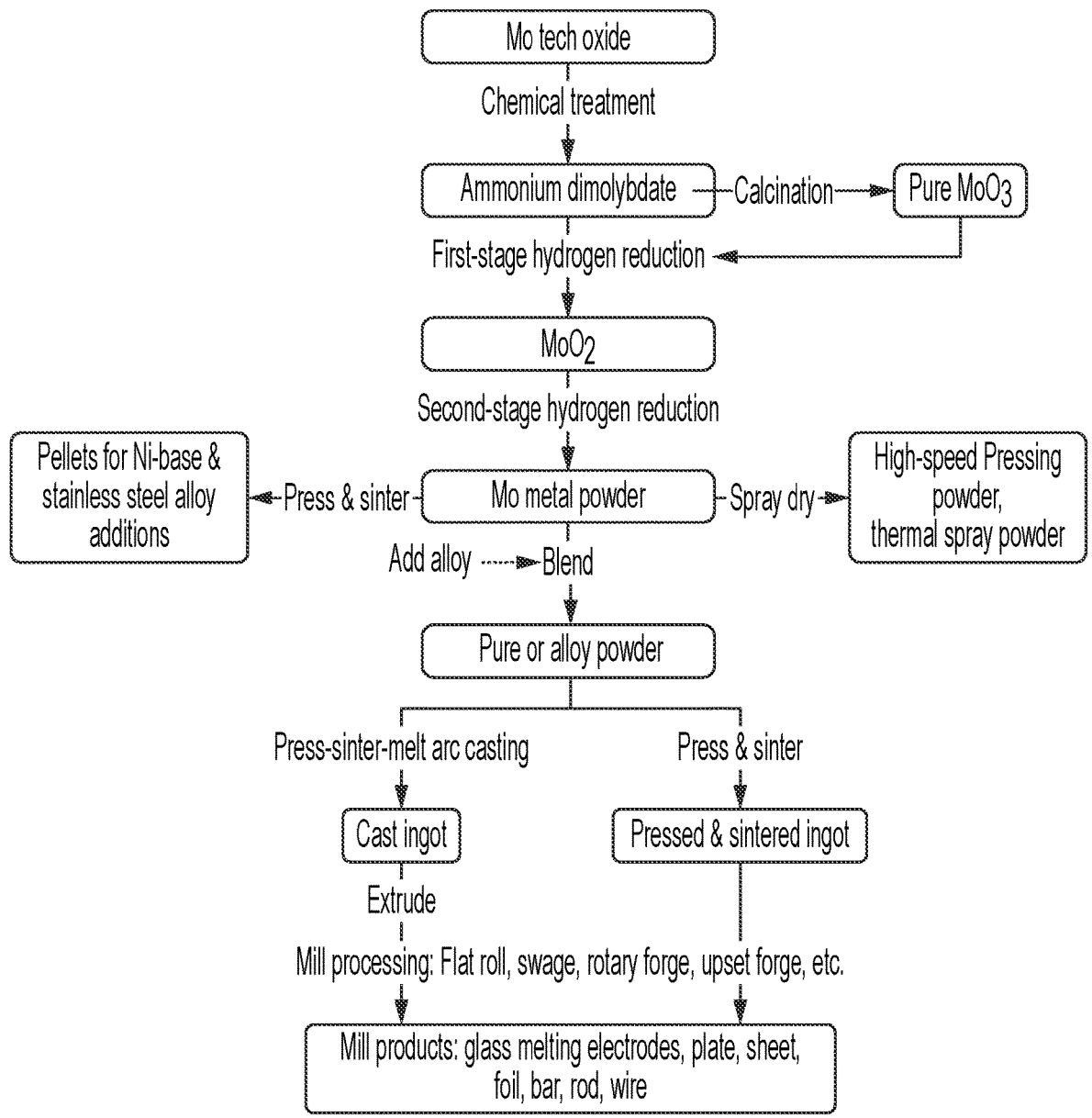
FIG. 31 shows a flowsheet describing the production of molybdenum metal mill product.

FIG. 31 shows a flow chart outlining an example production of molybdenum metal mill product. The flow refers in this example to melting processing for a refractory metal, such as Molybdenum (Mo) as a particular example.

Figure 32:
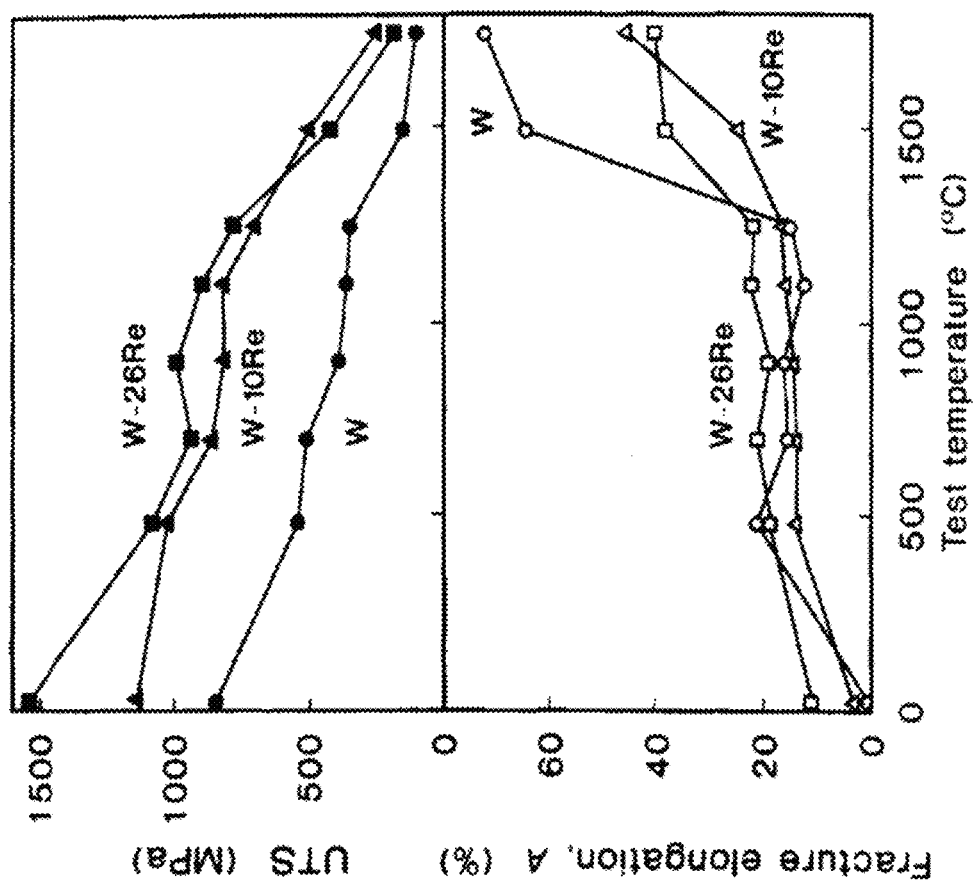
FIG. 32 shows the tensile properties, as a function of test temperature, of W and W-Re disks forged by 75%, measured in the radial direction.

FIG. 32 shows the tensile properties, as a function of test temperature, of W and W—Re disks forged by 75%, measured in the radial direction.

Figure 33:
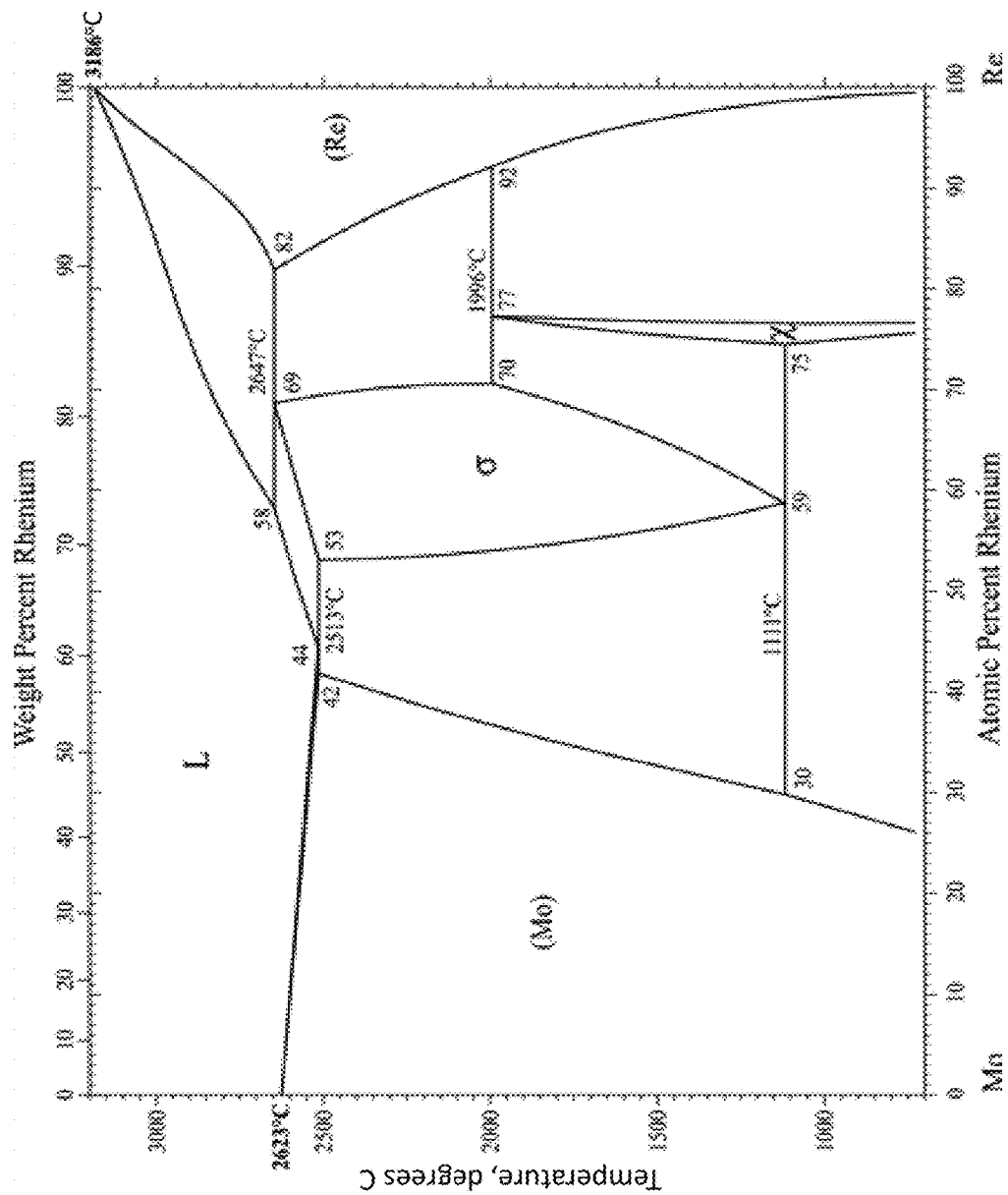
FIG. 33 shows phase diagram for of Molybdenum-Rhenium.

FIG. 33 shows phase diagram for of Molybdenum-Rhenium.

Figure 34:
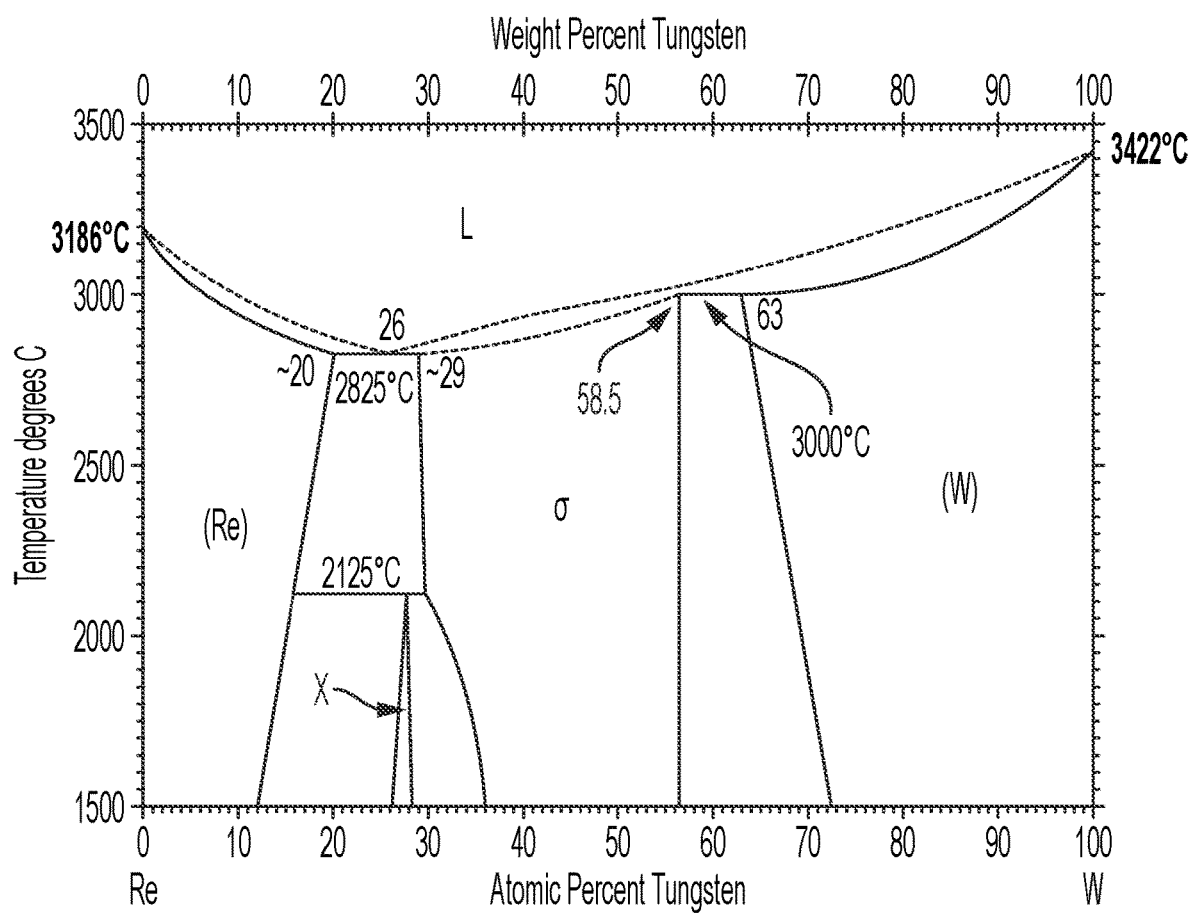
FIG. 34 shows a phase diagram for Tungsten-Rhenium.

FIG. 34 shows a phase diagram for Tungsten-Rhenium.

Figure 35:
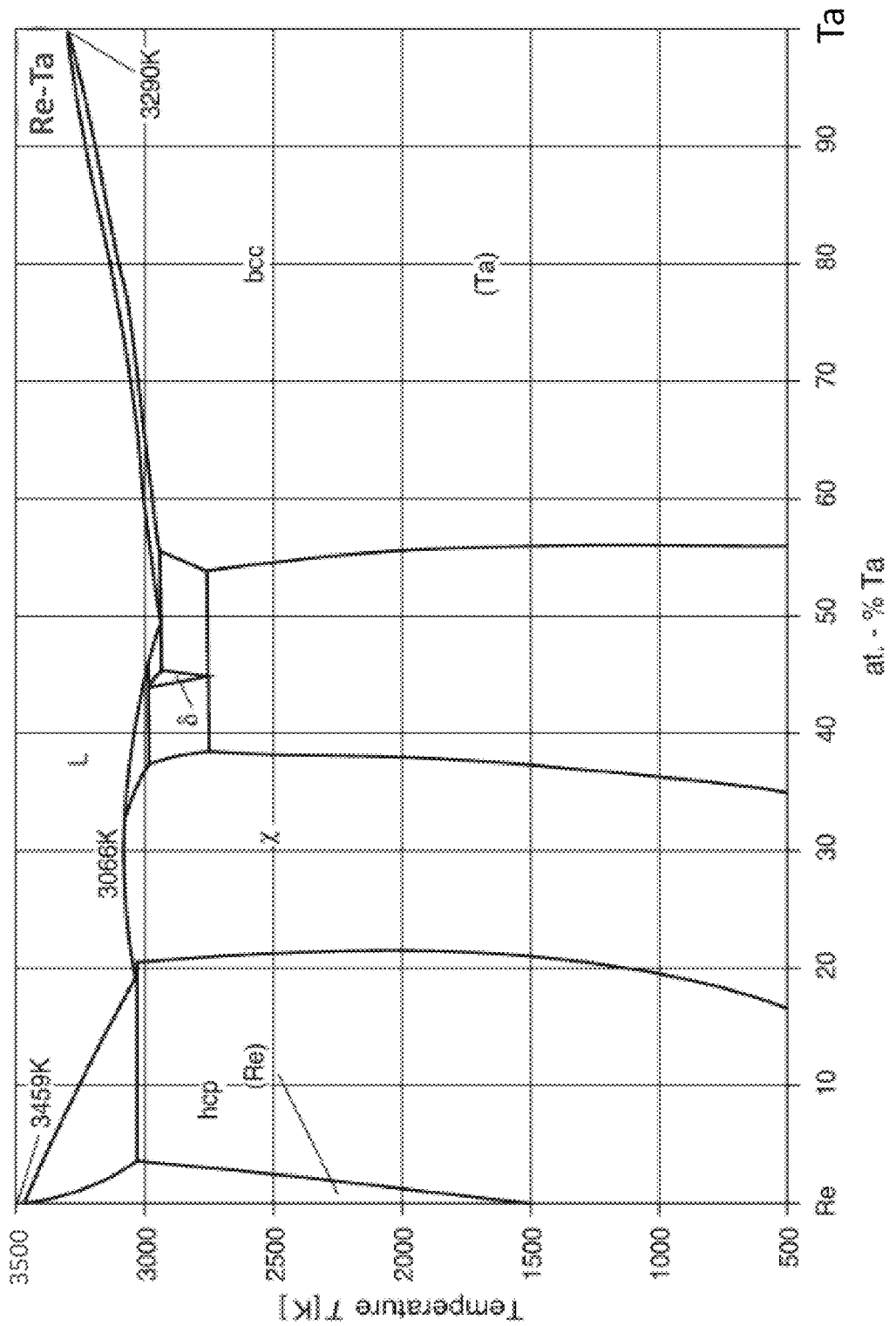
FIG. 35 shows a phase diagram for Rhenium-Tantalum.

FIG. 35 shows a phase diagram for Rhenium-Tantalum.

Figure 36:
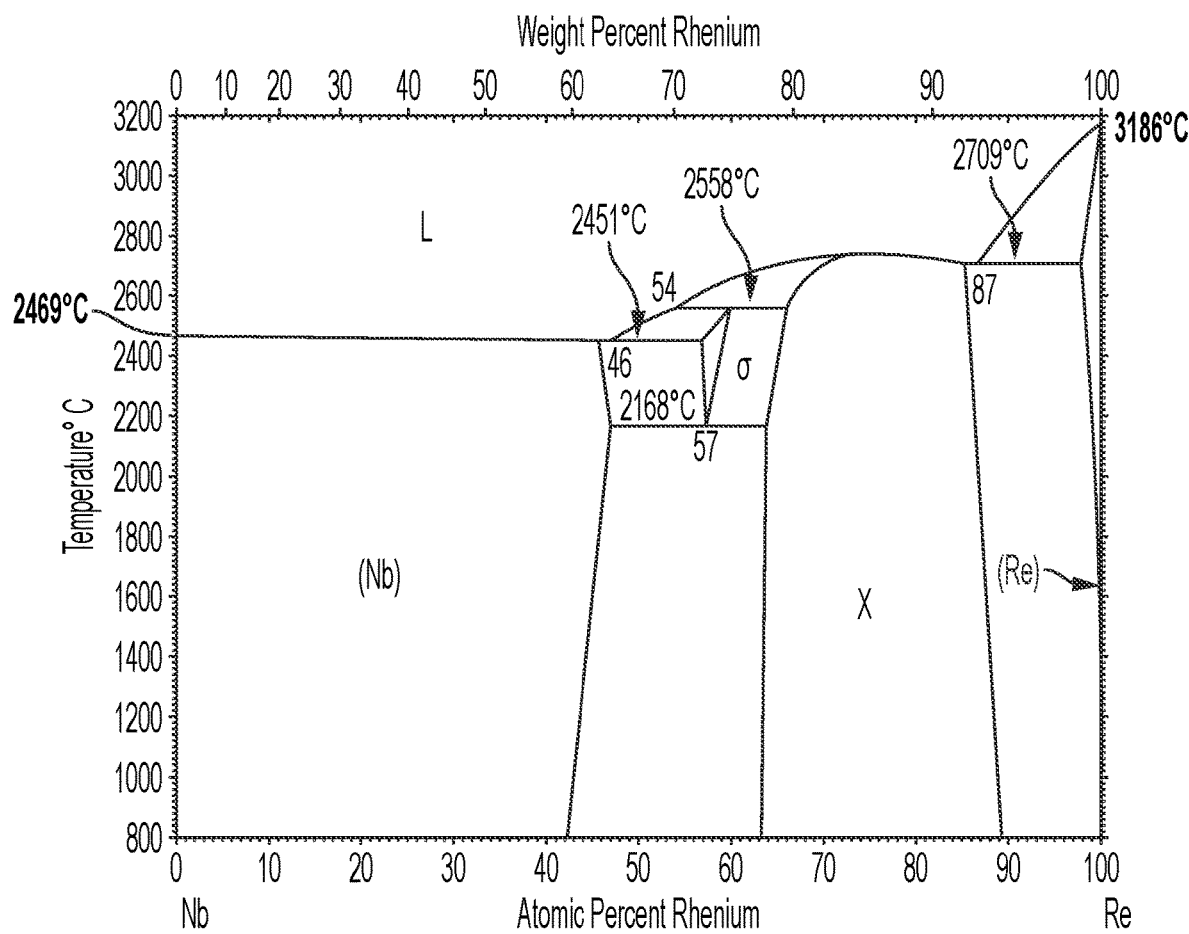
FIG. 36 shows a phase diagram for Rhenium-Niobium.

FIG. 36 shows a phase diagram for Rhenium-Niobium.

Figure 37:
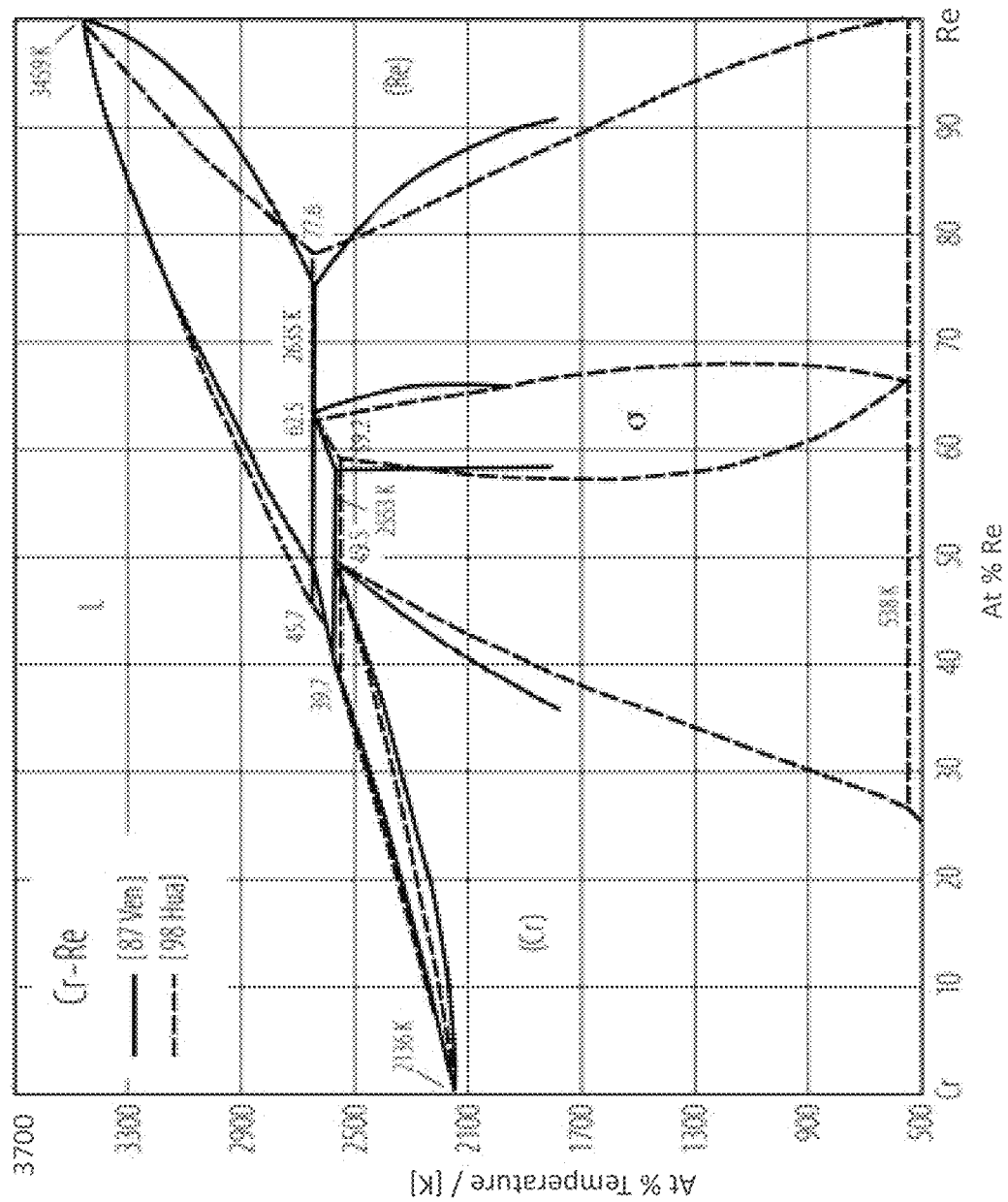
FIG. 37 shows a phase diagram for Rhenium-Chromium.

FIG. 37 shows a phase diagram for Rhenium-Chromium.

Figure 38:
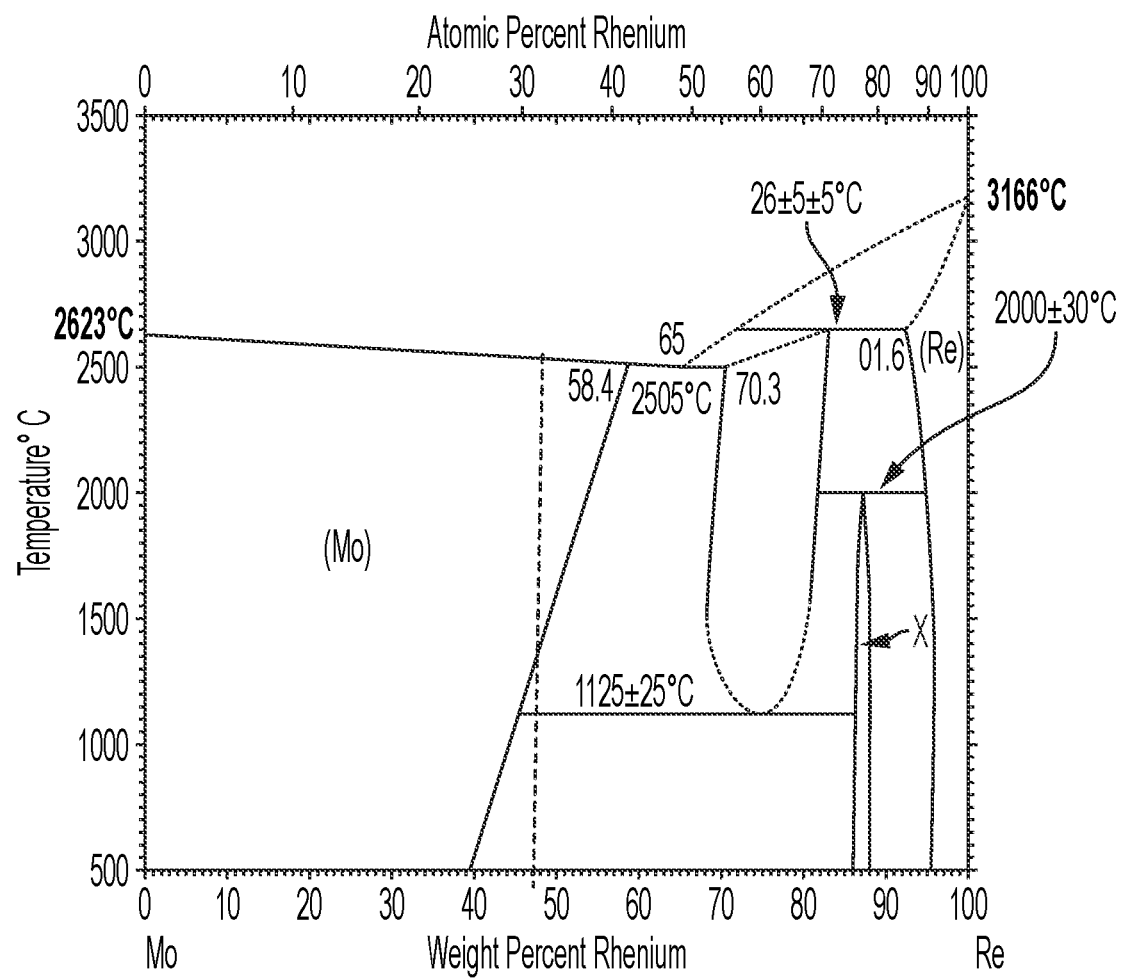
FIG. 38 shows properties of molybdenum 47.5% Rhenium.

FIG. 38 shows properties of molybdenum 47.5% Rhenium.

FIG. 39 is a table showing standard free energies of formation at 100K of some oxides having select metallic elements often present in superalloys.

REFERENCES

1. Tungsten Properties, Chemistry, Technology of the Element, Alloys, and Chemical Compounds Erik Lassner and Wolf-Dieter Schubert Vienna University of Technology Vienna, Austria Kluwer Academic/Plenum Publishers New York, Boston, Dordrecht, London, Moscow, 1998
2. DMIC Report 191 Sep. 27, 1963 V) 0.1~THE ENGINEERING PROPERTIES OF TUNGSTEN AND TUNGSTEN ALLOYS [DEFENSE METALS INFORMATION CENTER Battelle Memorial Institute Columbus 1, Ohio. F. F. Schmidt and H. R. Ogden
3. Alloys od molybdenum, rhenium, and tungsten, Int'l. Patent application Pun. No. WO93/16206, De Nemours, 1993
4. Felix et al. 54 ALLOYS OF MOLYBDENUM, RHENIUM AND TUNGSTEN Vinci M. Felix, Kennett Square, Pa.; Yong J. Park, Brossard, Canada E. I. Du Pont de Nemours and Company, Wilmington, Del. (21) Appl. No.: 87,947 (22 Filed: Jul. 6, 1993, Patent Number: 45 Date of Patent: U.S. Pat. No. 5,372,661 Dec. 13, 1994
5. Review Corrosion of Metallic Biomaterials: A Review Noam Eliaz Department of Materials Science and Engineering, Tel-Aviv University, Ramat Aviv 6997801, Israel; Materials, 2019
6. THE ENGINEERING PROPERTIES OF MOIYBDENUM AND MOLYBDENUM ALLOYS AD DEFENSE METALS INFORMATION CENTER 810tell0 Memorial Inilitlto Columbus 1. Ohio, DUJC xepart 190 TiE ENGINEERING PROPERTIES OF MOLYBDENUM AND MOLYBDENUM ALLOYS/by F. F. Schmidt and It. R. Ogden, 1963
7. CHEMICAL ENGINEERING TRANSACTIONS VOL. 41, 2014 A publication of The Italian Association of Chemical Engineering www.aidic.it/cet Guest Editors: Simonetta Palmas, Michele Mascia, Annalisa Vacca Copyright © 2014, AIDIC Servizi S.r.l., ISBN 978-88-95608-32-7; ISSN 2283-9216 Determination of Corrosion Rate of Rhenium and Its Alloys. Alexey D. Davydov*a, Vyacheslav S. Shaldaeva, Alexandra N. Malofeevaa, Oksana V. Chernyshovab, Vladimir M. Volgina, C.
8. TECHNICAL REPORT on THE EFFECT OF RHENIUM ON THE FABRIGABILITY AND DUCTILITY OF MOLYBDENUM AND TUNGSTEN to Department of The Navy Office of Naval Research Contract Nonr-1512 (00) by R. I. Jaffee and C. T. Sin&* April 1, 195
9. University of South Florida Scholar Commons Graduate Theses and Dissertations Graduate School 2013 Biomechanical Comparison of Titanium and Cobalt Chromium Pedicle Screw Rods in an Unstable Cadaveric Lumbar Spine James Doulgeris University of South Florida, 2013
10. The use of tungsten as a chronically implanted material Article in Journal of Neural Engineering January 2018 DOI: 10.1088/1741-2552/aaa502 CITATIONS 4 READS 292 2 authors: Some of the authors of this publication are also working on these related projects: CANDO Optogenetic Treatment of Epilepsy View project Ahmad Shah Idil University College London, 2018
11. Standard publications of the various binary phase diagrams.

Additional Summary of Select Alloys, Combinations, Implementations and the Like

In various embodiments the device includes a biocompatible refractory-metal-based alloy, having multiple refractory metals. The alloy may have an elastic modulus above 300 GPa. The refractory metals have a high-modulus tungsten. The refractory metals may include a high-modulus molybdenum; and The alloy includes high-modulus tungsten and high-modulus molybdenum.

The alloy in some embodiments includes at least one of the transition elements, including chromium (up to about 25 wt. %), and, additionally with tantalum, niobium, hafnium, zirconium, and titanium, and additionally, and yttrium in any amount, such as in the amount each of less than 5 weight percent.

The alloy in various embodiments is or includes a Molybdenum-Tungsten (Mo—W) alloy having some level of Chromium (Cr). The alloy can have any amount of any one or more of Tantalum (Ta), Columbium (Nb), Hafnium (Hf), and Titanium (Ti). The allow in some cases includes Zirconium (Zr). In some cases, the alloy includes Yttrium (Yt). One or more of these elements, such as Zr, can promote the benefits of Cr for embodiments in which Cr is included.

The alloy has one or more interstitial elements selected from a group consisting of as carbon, oxygen, hydrogen and nitrogen that should be less than 1500 PPM each.

The alloy can be free of ferromagnetic elements. The alloy is in various embodiments free of any of cobalt, nickel, and iron.

The alloy has passivity (corrosion resistance) in aqueous chloride environment similar to that of current implant metals and alloys, in various embodiments.

Tungsten is in various cases present in any desired amount or within any desired range, of the quantities outlined in the description above, including by table.

Molybdenum is in various embodiments present in any desired amount or within any desired range, of the quantities outlined in the description above, including by table.

The alloy in various embodiments includes an amount determined sufficient of molybdenum and tungsten (Mo+W) as a base alloy, in addition to other alloy elements, such that the alloy elastic modulus is greater than about 300 GPa. The alloy can have self passivation ability from the addition of Chromium (Cr), for instance, as well or instead by inclusion of any of Tantalum (Ta), Columbium (Nb), Hafnium (Hf), Titanium (Ti), etc. The alloy in some cases includes Zirconium (Zr). In some cases, the alloy includes Yttrium (Yt). One or more of these elements, such as Zr, can promote the benefits of Cr for embodiments in which Cr is included.

The transition elements are present in any desired amount or within any desired range, of the quantities outlined in the description above, including by table.

The device may be, e.g., an implant, such as a spinal implant, such as a rod, a screw, a screw head (e.g., receivers, or tulips, and any extenders or tabs connected thereto), a rod-to-rod connector, a plate. In various embodiments, the implant includes a high-modulus alloy for spinal disc replacement.

The implant may be a stent, such as a neurovascular or cardiovascular, or other cardiovascular or neurovascular devices, delivery devices or otherwise. The implant may be a guidewire that is more torque-responsive than convention guidewires. The implant may include a catheter.

The device may be a dental device, such as a dental implant.

The device is in some cases an orthopaedic device, such as an orthopaedic implant, such as a spinal or other bone-anchored or connected implant, including joint replacement devices, trauma devices, including plates and screws, Intramedulary nails, and the like.

The device may be an arthroscopic instrument device.

The device may be a medical cutting device.

The alloy is in various embodiments substantially free of ferromagnetic elements.

CONCLUSION

It should be understood that various aspects disclosed herein may be combined in combinations other than the combinations presented specifically in the description and the accompanying drawings. It should also be understood that, depending on the example, certain acts or events of any of the processes or methods described herein may be performed in other sequence, added, merged, or left out altogether (e.g., all described acts or events may not be necessary to carry out the techniques).

In addition, while certain aspects of this disclosure are described as being performed by a single module or unit for purposes of clarity, it should be understood that the techniques of this disclosure may be performed by a combination of units or modules associated with, for example, a medical device.

Unless defined specifically otherwise herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A medical device comprising:
    a biocompatible refractory-metal-based alloy, comprising multiple refractory metals;
    wherein the alloy has an elastic modulus above about 300 GPa;
    wherein the alloy comprises 30-35% tungsten and 60% molybdenum;
    wherein the alloy further comprises 5-10% niobium; and
    wherein the alloy is absent of rhenium.

2. The medical device of claim 1, wherein the alloy further comprises at least one of chromium, tantalum, hafnium, zirconium, titanium, and yttrium, in the amount each of less than 5 weight pct.

3. The medical device of claim 2, wherein the alloy further comprises carbon, oxygen, hydrogen and/or nitrogen.

4. The medical device of claim 1, wherein the alloy is free of ferromagnetic elements.

5. The medical device of claim 1, wherein the alloy is free of cobalt.

6. The medical device of claim 1, wherein the alloy is free of nickel.

7. The medical device of claim 1, wherein the alloy is free of iron.

8. The medical device of claim 1, wherein the alloy is free of cobalt, nickel, and iron.

9. The medical device of claim 1, wherein the device is an implant.

10. The medical device of claim 9, wherein the device is a spinal implant.

11. The medical device of claim 10, wherein the implant comprises a rod.

12. The medical device of claim 10, wherein the implant comprises a rod-to-rod connector.

13. The medical device of claim 10, wherein the implant comprises a plate.

14. The medical device of claim 10, wherein the implant comprises a bonescrew, rod-receiver, or screw assembly being a fixed, uni-axial, or multi-axial screw assembly.

15. The medical device of claim 9, wherein the implant comprises a stent.

16. The medical device of claim 15, wherein the stent is a cardiovascular stent.

17. The medical device of claim 15, wherein the stent is a neurovascular stent.

18. The medical device of claim 15, wherein the stent due to the alloy of the present technology has reduced recoil as compared to convention-material stents.

19. The medical device of claim 9, wherein the implant is a cardiovascular stent.

20. The medical device of claim 1, wherein the device is a dental device.

21. The medical device of claim 20, wherein the device is a dental implant.

22. The medical device of claim 1, wherein the device is an orthopaedic device.

23. The medical device of claim 22, wherein the orthopaedic device is an orthopaedic implant.

24. The medical device of claim 23, wherein the orthopaedic implant is a spinal implant.

25. The medical device of claim 1, wherein the device is an arthroscopic or cutting device.

26. The medical device of claim 1, wherein the device is a medical cutting device.

27. The medical device of claim 1, wherein the device is an orthopaedic joint replacement device.

28. The medical device of claim 1, wherein the device is an orthopaedic trauma device.

29. The medical device of claim 1, wherein the device is a cardiovascular device.

30. The medical device of claim 1, wherein the device is a neurovascular device.

31. The medical device of claim 30, wherein the device is a neurovascular guidewire.

32. The medical device of claim 1, wherein the device is a torque-responsive medical delivery device.

33. The medical device of claim 1, wherein the device is a spinal interbody.

34. The medical device of claim 1, wherein the device is a spinal disc replacement.

35. The medical device of claim 1, wherein the alloy is free of ferromagnetic elements.

* * * * *